US009232902B2

(12) United States Patent
Takahashi et al.

(10) Patent No.: US 9,232,902 B2
(45) Date of Patent: Jan. 12, 2016

(54) DETECTION CIRCUIT FOR GENERATING BIOLOGICAL INFORMATION

(71) Applicant: MURATA MANUFACTURING CO., LTD., Nagaokakyo-Shi, Kyoto-Fu (JP)

(72) Inventors: Eiji Takahashi, Nagaokakyo (JP); Noriaki Okuda, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 280 days.

(21) Appl. No.: 13/865,391

(22) Filed: Apr. 18, 2013

(65) Prior Publication Data
US 2014/0142447 A1 May 22, 2014

Related U.S. Application Data
(63) Continuation of application No. PCT/JP2011/073394, filed on Oct. 12, 2011.

(30) Foreign Application Priority Data

Oct. 27, 2010 (JP) .................................. 2010-240665
May 19, 2011 (JP) .................................. 2011-112520

(51) Int. Cl.
| H03G 3/30 | (2006.01) |
| A61B 5/0428 | (2006.01) |
| H03F 3/45 | (2006.01) |
| H03G 1/00 | (2006.01) |
| A61B 5/04 | (2006.01) |
| A61B 5/0408 | (2006.01) |
| A61B 5/00 | (2006.01) |

(52) U.S. Cl.
CPC ........... *A61B 5/04284* (2013.01); *A61B 5/0408* (2013.01); *A61B 5/04012* (2013.01);
(Continued)

(58) Field of Classification Search
CPC ............... A61B 5/0402; A61B 5/0452; A61B 5/04012; A61B 5/0408; H03F 3/602; H03F 3/211; H03F 3/45475; G01R 17/02; H03G 3/30
USPC ....... 600/509; 330/124, 144, 147, 148, 124 R
See application file for complete search history.

(56) References Cited

U.S. PATENT DOCUMENTS

| 4,859,964 A | 8/1989 | Jorgensen |
| 5,002,063 A * | 3/1991 | Haner .................. A61B 5/0428 600/509 |

(Continued)

FOREIGN PATENT DOCUMENTS

| JP | 60-103937 A | 6/1985 |
| JP | 63-502473 A | 9/1988 |

(Continued)

OTHER PUBLICATIONS

International Search Report and Written Opinion for International Application No. PCT/JP2011/073394, mailed Dec. 27, 2011.

*Primary Examiner* — Christopher D Koharski
*Assistant Examiner* — Michael Carey
(74) *Attorney, Agent, or Firm* — Arent Fox LLP

(57) ABSTRACT

An amplifier circuit includes first and second amplification units. A first detection electrode and a high impedance circuit are connected to the input terminal of the first amplification unit. A second detection electrode and a high impedance circuit are connected to the input terminal of the second amplification unit. The output terminals of the first and second amplification units output first and second output signals, and are connected to the input terminals of a differential amplifier circuit through coupling capacitors, respectively. The differential amplifier circuit operates a difference between the first and second output signals in a state where a direct-current component is omitted.

14 Claims, 10 Drawing Sheets

(52) U.S. Cl.
CPC .......... *A61B5/7246* (2013.01); *H03F 3/45475* (2013.01); *H03G 1/0035* (2013.01); *H03G 3/30* (2013.01); *H03F 2200/261* (2013.01); *H03F 2200/411* (2013.01); *H03F 2203/45522* (2013.01); *H03F 2203/45528* (2013.01)

(56) References Cited

U.S. PATENT DOCUMENTS

| | | |
|---|---|---|
| 7,782,131 B2 | 8/2010 | Nishizawa |
| 2001/0050625 A1 | 12/2001 | Piirainen et al. |
| 2009/0134940 A1* | 5/2009 | Nishizawa ................ H03F 1/34 330/149 |

FOREIGN PATENT DOCUMENTS

| | | |
|---|---|---|
| JP | 05-115452 A | 5/1993 |
| JP | 2003-168932 A | 6/2003 |
| JP | 2003-235823 A | 8/2003 |
| JP | 2004-241912 A | 8/2004 |
| JP | 2005-348440 A | 12/2005 |
| JP | 2007-504917 A | 3/2007 |
| WO | WO-2007/029737 A1 | 3/2007 |

* cited by examiner

DETECTION CIRCUIT FOR GENERATING BIOLOGICAL INFORMATION

CROSS REFERENCE TO RELATED APPLICATIONS

The present application is a continuation of International Application No. PCT/JP2011/073394 filed Oct. 12, 2011, which claims priority to Japanese Patent Application No. 2010-240665, filed Oct. 27, 2010, and to Japanese Patent Application No. 2011-112520, filed on May 19, 2011, the entire contents of each of which are incorporated herein by reference.

FIELD OF THE INVENTION

The present invention relates to a detection circuit subjecting a weak detection signal to differential arithmetic processing, for example, a detection circuit suitable for generating biological information such as an electrocardiogram on the basis of a detection signal (the electromotive force of a heart) serving as a weak voltage waveform appearing, owing to the electrical activity of the heart, in the body surface of a person to be measured.

BACKGROUND OF THE INVENTION

There has been known a measurement device that detects detection signals in body surfaces at at least two points in a person to be measured and measures biological information such as an electrocardiogram on the basis of a difference between the two detection signals. The measurement device includes at least two detection electrodes used for detecting detection signals and a detection circuit including a differential amplifier subjecting at least two detection signals, detected by the detection electrodes, to differential arithmetic processing (refer to Patent Document 1 or 2).

CITATION LIST

Patent Document

Patent Document 1: Japanese Unexamined Patent Application Publication No. 5-115452
Patent Document 2: Japanese Unexamined Patent Application Publication (Translation of PCT Application) No. 2007-504917

In a detection circuit described in Patent Document 1, a coupling capacitor is provided on the output side of a differential amplifier connected to two detection electrodes, and a direct-current voltage component within a differentially amplified detection signal is removed. In addition, a change in contact resistance between the body surface of a person to be measured and the detection electrodes or a direct-current voltage change amount caused by a change in a direct-current voltage component in the body surface of the person to be measured is superimposed on the detection signal detected by the detection electrode. Therefore, a difference between the direct-current voltage components superimposed on the two detection signals is also amplified by the differential amplifier. Accordingly, if the amplification factor of the differential amplifier is set high, a signal amplitude greater than or equal to an output bound occurs depending on the magnitude of the difference between the direct-current voltage components superimposed on the detection signals. Therefore, in some cases, a signal waveform is clamped or distortion occurs, and hence, it may be difficult to output a correct signal.

In addition, in a detection circuit described in Patent Document 2, coupling capacitors are individually provided between two detection electrodes and a differential amplifier, and a direct-current voltage component within each detection signal detected in each detection electrode is removed. However, between the coupling capacitor and the input portion of the differential amplifier, a resistance element or a capacitor is connected. Therefore, depending on the characteristic variations of these electronic components, in some cases a difference occurs between the direct-current voltage components within the individual detection signals. Such a difference between the direct-current voltage components within the individual detection signals is also amplified by the differential amplifier. Accordingly, in the same way as the detection circuit according to Patent Document 1, if the amplification factor of the differential amplifier is set high, a signal amplitude greater than or equal to an output bound occurs depending on the difference between the direct-current voltage components within the individual detection signals. Therefore, in some cases, a signal waveform is clamped or distortion occurs, and hence, it may be difficult to output a correct signal.

SUMMARY OF THE INVENTION

For example, in view of such a problem as described above, the present invention is made, and an object of the present invention is to provide a detection circuit used for subjecting two detected weak detection signals to differential arithmetic processing.

(1). In view of the above-mention problem, the present invention provides a detection circuit including an amplifier circuit including at least a first amplification unit and a second amplification unit, and a differential circuit outputting a differential signal between a first output signal amplified in the first amplification unit and a second output signal amplified in the second amplification unit, wherein an input terminal of the first amplification unit is connected to a first detection electrode, and connected on one end side of a first high impedance circuit whose other end side is connected to a reference measurement electric potential, an input terminal of the second amplification unit is connected to a second detection electrode, and connected on one end side of a second high impedance circuit whose other end side is connected to the reference measurement electric potential, an output terminal of the first amplification unit and a first input terminal of the differential circuit are connected to each other through a first coupling capacitor, and an output terminal of the second amplification unit and a second input terminal of the differential circuit are connected to each other through a second coupling capacitor.

According to the present invention, a configuration is adopted where one end side of the first high impedance circuit whose other end side is connected to the reference measurement electric potential is connected between the input terminal of the first amplification unit and the first detection electrode and one end side of the second high impedance circuit whose other end side is connected to the reference measurement electric potential is connected between the input terminal of the second amplification unit and the second detection electrode. Therefore, impedances when the input terminal sides of the first and second amplification units are individually viewed from the first and second detection electrodes become high impedances. Accordingly, since it is difficult for a detection signal to leak into the high impedance circuit, it is possible to detect even a weak detection signal. In addition, since the reference potentials of the input terminals of the first and second amplification units are fixed to a given electric potential, the fluctuations of the central potentials of the first and second detection signals become small. Accordingly, an SN ratio (Signal to Noise Ratio) is improved, and it is possible to stably detect the detection signal.

In addition, a configuration is adopted where the output terminal of the first amplification unit and the first input terminal of the differential circuit are connected to each other through the first coupling capacitor and the output terminal of the second amplification unit and the second input terminal of the differential circuit are connected to each other through the second coupling capacitor. Accordingly, owing to the first coupling capacitor, a direct-current voltage component is removed from the first output signal amplified by the first amplification unit. In addition, owing to the second coupling capacitor, a direct-current voltage component is removed from the second output signal amplified by the second amplification unit. After that, differential arithmetic processing is performed on the output signals from which the direct-current voltage components have been removed. Therefore, even if the amplification factors of the first and second amplification units are set high and the direct-current voltage components superimposed on the first and second detection signals are amplified, it is possible to remove the direct-current voltage components owing to the first and second coupling capacitors. Therefore, a signal waveform is not clamped, and distortion does not occur. As a result, a common-mode-noise cancelling performance is enhanced, and it is possible to obtain a differentially amplified signal that is desired for detection and correct.

(2). Further, in the present invention, a configuration is adopted where the first and second amplification units in the amplifier circuit and the differential circuit are configured using operational amplifiers and the first amplification unit and the second amplification unit individually set amplification factors of the operational amplifiers therein so that, within a range of a driving voltage causing the operational amplifier in the differential circuit to operate, the first and second output signals become values near to a maximum value of the driving voltage.

According to the present invention, since the amplification factors of the first and second amplification units are set high so that, within the range of a driving voltage causing the operational amplifier in the differential circuit to operate, the first and second output signals become values near to a maximum value of the driving voltage, and the amplification factor of the differential circuit is set relatively low with respect to the amplification factors of the first and second amplification units, it is possible to improve the SN ratio of the detection circuit.

(3). In addition, in the present invention, a configuration is adopted where an output terminal of the differential circuit is connected to an A/D converter circuit having a preliminarily defined input level, the first and second amplification units in the amplifier circuit and the differential circuit are configured using operational amplifiers, and the first amplification unit and the second amplification unit individually set amplification factors of the operational amplifiers therein so that, within a range lower than the input level of the A/D converter circuit, the first and second output signals become values near to the input level.

According to the present invention, since the amplification factors of the first and second amplification units are set high so that, within a range lower than the input level of the A/D converter circuit, the output signals of the detection circuit become values near to the input level, and the amplification factor of the differential circuit is set relatively low with respect to the amplification factors of the first and second amplification units, it is possible to improve the SN ratio of the detection circuit. In addition, it is possible to improve the degree of accuracy when an analog signal is quantized and discretized into a digital signal by the A/D converter circuit.

(4). In the present invention, a configuration is adopted where, in the first amplification unit and the second amplification unit in the amplifier circuit, an automatic gain control circuit is provided that controls an amplification factor of the first amplification unit and an amplification factor of the second amplification unit on the basis of a feedback signal based on the differential signal of the differential circuit.

According to the present invention, since the automatic gain control circuit is provided in the first and second amplification units in the amplifier circuit, the amplification factors of the first and second amplification units are controlled on the basis of the feedback signal based on the differential signal from the differential circuit. Therefore, even if the magnitude of the detection signal has changed, the amplification factors of the first and second amplification units are varied, and hence, it is possible to detect in an optimum state.

(5). In the present invention, a configuration is adopted where, in the first amplification unit and the second amplification unit in the amplifier circuit, an automatic gain control circuit is provided that controls an amplification factor of the first amplification unit and an amplification factor of the second amplification unit on the basis of a feedback signal based on the differential signal of the differential circuit, an output terminal of the differential circuit is connected to a digital processing circuit, and the digital processing circuit includes an A/D converter circuit configured to convert, into a digital signal, a differential signal including an analog signal output from the differential circuit, a maximum value detection means configured to sequentially detect a maximum value in the digital signal output from the A/D converter circuit, with respect to each of successive sampling times, a determination time reset means configured to update a maximum value to a new maximum value, resets a preliminarily defined determination time, and times again the determination time from a time at which the new maximum value has been detected when the new maximum value larger than the maximum value detected by the maximum value detection means has been detected within the determination time from a time at which the maximum value had been detected, a peak value determination means configured to determine the maximum value as a peak value when no new maximum value larger than the maximum value detected by the maximum value detection means is detected within the determination time from a time at which the maximum value has been detected, and a comparison means configured to compare a difference between the peak value obtained by the peak value determination means and a reference value based on the reference measurement electric potential with at least one threshold value preliminarily set, wherein when the comparison means has determined that the difference between the peak value and the reference value is larger than the threshold value, the automatic gain control circuit outputs the feedback signal decreasing an amplification factor of the first amplification unit and an amplification factor of the second amplification unit, and when the comparison means has determined that the difference between the peak value and the reference value is smaller than the threshold value, the automatic gain control circuit outputs the feedback signal increasing the amplification factor of the first amplification unit and the amplification factor of the second amplification unit.

According to the present invention, since the automatic gain control circuit is provided in the first and second amplification units in the amplifier circuit, the amplification factors of the first and second amplification units are controlled on the basis of the feedback signal based on the differential signal from the differential circuit. In addition, the output terminal of the differential circuit is connected to the digital processing circuit, and the digital processing circuit adopts a configuration including the A/D converter circuit, the maximum value detection means, the determination time reset means, the peak value determination means, and the comparison means. In this case, the differential signal including the analog signal is converted into the digital signal by the A/D converter circuit, and the maximum value of the digital signal acquired with respect to each sampling time is detected by the maximum value detection mechanism means. In addition, when the new maximum value larger than the detected maximum value has been detected by the maximum value detection means within the determination time, the maximum value is updated and the determination time is reset, owing to the determination time reset means. On the other hand, when no new maximum value larger than the detected maximum value is detected by the maximum value detection means within the determination time, the maximum value detected by the maximum value detection means is determined as the peak value, owing to the peak value determination means.

In addition, the comparison means compares a difference between the peak value and the reference value with at least one threshold value preliminarily set. In addition, when the difference between the peak value and the reference value is larger than the threshold value, the automatic gain control circuit outputs the feedback signal decreasing the amplification factor of the first amplification unit and the amplification factor of the second amplification unit. On the other hand, when the difference between the peak value and the reference value is smaller than the threshold value, the automatic gain control circuit outputs the feedback signal increasing the amplification factor of the first amplification unit and the amplification factor of the second amplification unit. In this way, even if the difference between the peak value and the reference value has changed, the amplification factors of the first and second amplification units are varied. Therefore, it is possible to detect the differential signal in a suitable state.

(6). In the present invention, a configuration is adopted where the digital processing circuit includes a sequential change means configured to sequentially change the determination time in response to a time interval between the peak values.

According to the present invention, a configuration is adopted where the digital processing circuit includes the sequential change means configured to sequentially change the determination time in response to a time interval between the peak values. Therefore, for example, even if the differential signal is detected where the period of the peak value fluctuates as the rhythmic period of the beat of a living body, which sequentially fluctuates, it is possible to prevent the determination time from extending over a plurality of periods, by sequentially changing the determination time in response to the fluctuation of the period, and it is possible to reliably determine the peak value.

DETAILED DESCRIPTION OF THE PREFERRED EMBODIMENTS OF THE INVENTION

Hereinafter, in accordance with accompanying drawings, a detection circuit according to an embodiment of the present invention will be described with citing, as an example, a case of being applied to a measurement device for biological information. In addition, the measurement device detects a detection signal serving as a weak voltage waveform occurring owing to the electrical activity of a heart, through a detection electrode directly attached to the body surface of the four limbs, the breast region, or the like of a person to be measured, and generates biological information such as an electrocardiogram, on the basis of the detection signal.

Figure 1:
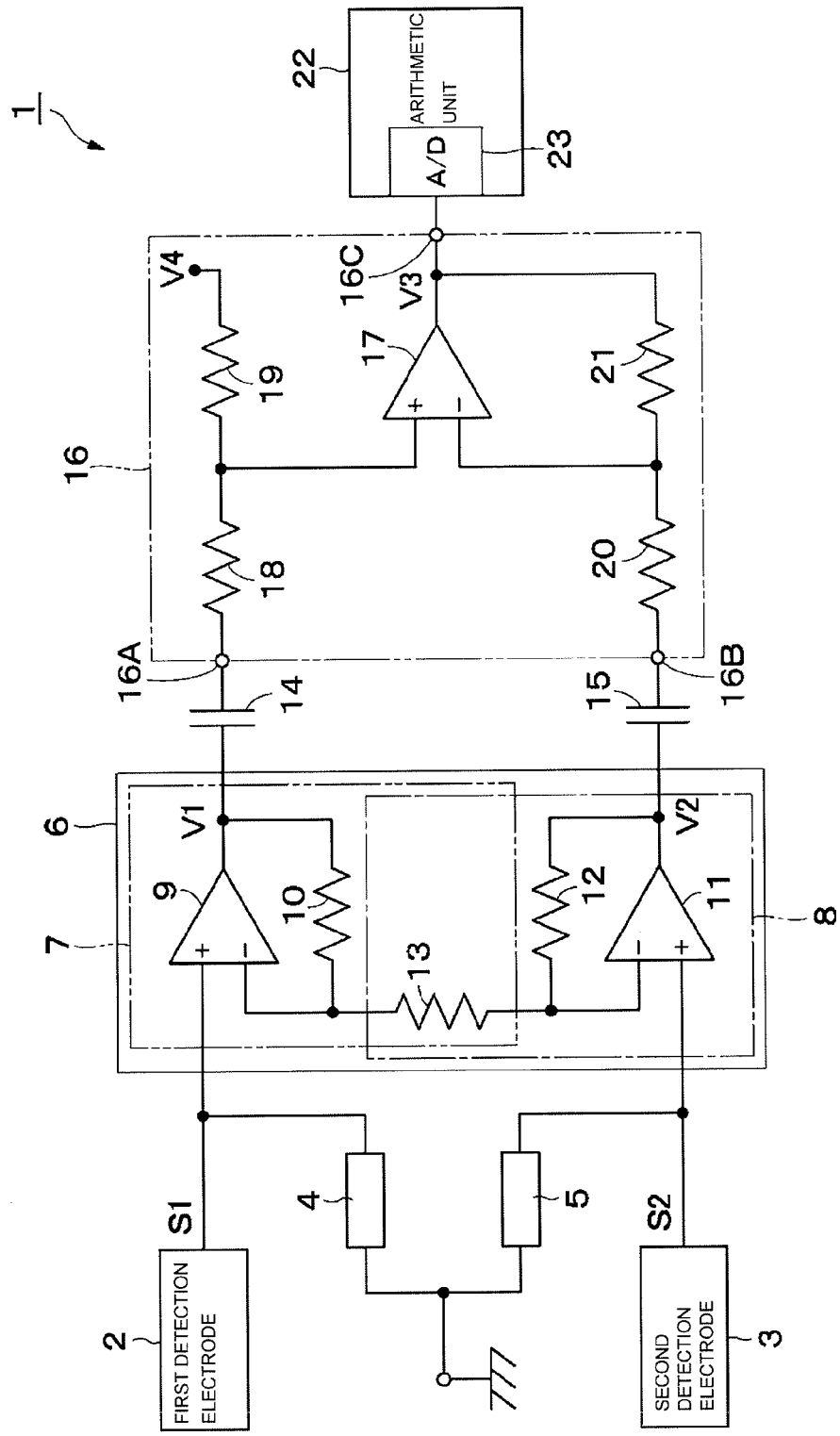
FIG. 1 is a circuit diagram illustrating a measurement device for biological information according to a first embodiment.

A first embodiment of the present invention is illustrated in FIG. 1. A measurement device 1 includes first and second detection electrodes 2 and 3, first and second high impedance circuits 4 and 5, an amplifier circuit 6, first and second coupling capacitors 14 and 15, a differential amplifier circuit 16, and an arithmetic unit 22.

The first and second detection electrodes 2 and 3 are formed using, for example, a conductive film including a conductive metal material or a conductive resin material. The first and second detection electrodes 2 and 3 are attached in a state of being in direct contact with the different body surfaces of the person to be measured. The first detection electrode 2 detects a first detection signal S1 serving as an analog signal, from a first body surface. In addition, the second detection electrode 3 detects a second detection signal S2 serving as an analog signal, from a second body surface.

The first high impedance circuit 4 is configured using, for example, a high-resistance element having high impedance greater than or equal to several MΩ. One end side of the first high impedance circuit 4 is connected to the first detection electrode 2, and connected to the non-inverting terminal of an operational amplifier 9 configuring the amplifier circuit 6 described later. The second high impedance circuit 5 is configured in substantially the same way as the first high impedance circuit 4, and has high impedance greater than or equal to, for example, several MΩ. One end side of the second high impedance circuit 5 is connected to the second detection electrode 3, and connected to the non-inverting terminal of an operational amplifier 11 configuring the amplifier circuit 6 described later. The other end sides of the first and second high impedance circuits 4 and 5 are subjected to common connection, and connected to, for example, a ground potential serving as a reference measurement electric potential.

In addition, while a case has been illustrated where the other end sides of the first and second high impedance circuits 4 and 5 are connected to the ground potential, the reference measurement electric potential is not limited to the ground potential, and may also be an electric potential whose fluctuation is small, for example, as the electric potential of a foot of the person to be measured. In addition to this, the reference measurement electric potential may also be a given direct-current potential if the direct-current potential falls within the range of the driving voltage of an amplifier. In addition, when the given direct-current potential is set to an intermediate potential falling within the range of the driving voltage of the amplifier, a signal waveform fluctuates with this intermediate potential as the center, and hence, effective amplification becomes easily performed.

In addition, the first and second high impedance circuits 4 and 5 not only adopts a configuration where high-resistance elements are used but may also adopt a configuration where, for example, a pair of diodes is series-connected so that the individual forward directions thereof are caused to face directions opposite to each other. In this case, the impedances of the first and second high impedance circuits 4 and 5 become greater than or equal to, for example, 100 MΩ.

In addition, a configuration may also be adopted where, as the first and second high impedance circuits 4 and 5, high-resistance semiconductor films such as, for example, oxides, are used that are formed owing to a sputtering method, a CVD method, an MBE method, a vapor deposition method.

The amplifier circuit 6 includes a first amplification unit 7 and a second amplification unit 8. The first amplification unit 7 is configured using the operational amplifier 9 (Op-amp), and the output terminal and the inverting terminal of the operational amplifier 9 are connected to each other through a resistor 10. The non-inverting terminal of the operational amplifier 9 is connected to a common connection point between the first detection electrode 2 and the high impedance circuit 4. In substantially the same way as the first amplification unit 7, the second amplification unit 8 is configured using the operational amplifier 11 (Op-amp), and the output terminal and the inverting terminal of the operational amplifier 11 are connected to each other through a resistor 12. The non-inverting terminal of the operational amplifier 11 is connected to a common connection point between the second detection electrode 3 and the high impedance circuit 5. In addition, the inverting terminals of the operational amplifier 9 and the operational amplifier 11 are connected to each other through a resistor 13.

As a result, the first amplification unit 7 configures a non-inverting amplifier circuit using the operational amplifier 9 and the resistors 10 and 13, and amplifies the first detection signal S1 to output a first output signal V1. In addition, the amplification factor thereof depends on the resistance values of the resistors 10 and 13. In addition, the second amplification unit 8 configures a non-inverting amplifier circuit using the operational amplifier 11 and the resistors 12 and 13, and amplifies the second detection signal S2 to output a second output signal V2. In addition, the amplification factor thereof depends on the resistance values of the resistors 12 and 13.

The first coupling capacitor 14 is connected between the output terminal of the first amplification unit 7 and the first input terminal 16A of the differential amplifier circuit 16 described later. The second coupling capacitor 15 is connected between the output terminal of the second amplification unit 8 and the second input terminal 16B of the differential amplifier circuit 16.

The differential amplifier circuit 16 includes an operational amplifier 17 (Op-amp). The non-inverting terminal of the operational amplifier 17 is connected to a connection point between a resistor 18 and a resistor 19 connected in series. The other end of the resistor 18 is connected to the first input terminal 16A. The other end of the resistor 19 is connected to a given direct-current potential V4 falling within the range of the driving voltage Vdd of the operational amplifier 17. In other words, the non-inverting terminal of the operational amplifier 17 is connected through the resistor 19 to a given direct-current potential falling within the range of the driving voltage Vdd of the operational amplifier 17. In addition, if the given direct-current potential is set to an intermediate potential falling within the range of the driving voltage of the amplifier, a signal waveform fluctuates with this intermediate potential as the center, and hence, effective amplification becomes easily performed.

The inverting terminal of the operational amplifier 17 is connected to a connection point between a resistor 20 and a resistor 21 connected in series. The other end of the resistor 20 is connected to the second input terminal 16B. The other end of the resistor 21 is connected to the output terminal of the operational amplifier 17. The differential amplifier circuit 16 differentially amplifies an input signal from the first input terminal 16A and an input signal from the second input terminal 16B, and outputs a differentially amplified signal V3 from the output terminal 16C of the operational amplifier 17. In addition, the amplification factor of the differential amplifier circuit 16 depends on the resistance values of the resistors 18 to 21.

The arithmetic unit 22 is connected to the output terminal of the operational amplifier 17 serving as the output terminal 16C of the differential amplifier circuit 16, and calculates biological information such as an electrocardiogram on the basis of the differentially amplified signal V3. The arithmetic unit 22 includes a microcomputer, and on the input side thereof, an A/D converter circuit 23 is provided. The A/D converter circuit 23 has a preliminarily set input level, and subjects an analog signal ranging to this input level, to quantization and discretization to convert the analog signal into a digital signal. In addition, this input level is set to, for example, the same value as the driving voltage Vdd. The arithmetic unit 22 performs various kinds of arithmetic processing on the basis of the differentially amplified signal V3 converted into a digital signal by the A/D converter circuit 23, namely, the output signal of the detection circuit.

The measurement device 1 according to the present embodiment includes such a configuration as described above, and next the operation thereof will be described.

After the first and second detection electrodes 2 and 3 have been attached to the body surfaces of the person to be measured, when a switch (not illustrated) used for measurement start is put into ON, the first and second detection signals S1 and S2 are detected through the first and second detection electrodes 2 and 3.

At this time, since the first high impedance circuit 4 is connected to the first detection electrode 2 and the second high impedance circuit 5 is connected to the second detection electrode 3, impedances when a first amplification unit 7 side is viewed from the first detection electrode 2 and when a second amplification unit 8 side is viewed from the second detection electrode 3 are put into high impedances. In addition, since the other end sides of the first and second high impedance circuits 4 and 5 are connected to the ground potential, the input terminals of the first and second amplification units 7 and 8 are fixed to a given electric potential (ground potential). Therefore, it is possible to reliably input the first and second detection signals S1 and S2 into the first and second amplification units 7 and 8 and amplify the first and second detection signals S1 and S2. In addition, when the first and second detection signals S1 and S2 are amplified by the first and second amplification units 7 and 8, since the fluctuation of a central potential becomes small, an SN ratio is improved and stabilized.

The first amplification unit 7 amplifies the first detection signal S1, and outputs the first output signal V1. The second amplification unit 8 amplifies the second detection signal S2, and outputs the second output signal V2. The first output signal V1 is input to the first input terminal 16A of the differential amplifier circuit 16 through the first coupling capacitor 14. The second output signal V2 is input to the second input terminal 16B of the differential amplifier circuit 16 through the second coupling capacitor 15.

At this time, in some cases, direct-current voltage components are superimposed on the first and second detection signals S1 and S2, and thus on the first and second output signals V1 and V2, depending on changes in contact resistance between the body surfaces of the person to be measured and the first and second detection electrodes 2 and 3, changes in direct-current voltage components in the body surfaces of the person to be measured, or the characteristic variation of an electronic component used for the first or second high impedance circuit 4 or 5 or the amplifier circuit 6. However, the first and second coupling capacitors 14 and 15 are provided, and hence, direct-current voltage components happening to be superimposed on the first and second output signals V1 and V2 are preliminarily removed before being differentially amplified. As a result, in the differential amplifier circuit 16, the first and second output signals V1 and V2 are differentially amplified where the direct-current voltage components have been removed.

In addition, in a case where the first and second coupling capacitors 14 and 15 are connected between, for example, the first and second amplification units 7 and 8 and the end sides of the first and the second high impedance circuits 4 and 5, respectively, electric potentials on the input sides of the first and second amplification units 7 and 8 become unstable, and the operational amplifiers 9 and 11 do not normally function. In addition, in a case where the first and second coupling capacitors 14 and 15 are connected between the first and second detection electrodes 2 and 3 and the end sides of the first and second high impedance circuits 4 and 5, respectively, a difference between direct-current voltage components superimposed on the first and second detection signals S1 and S2 becomes large owing to the variations of the first and second high impedance circuits 4 and 5. A large difference between direct-current voltage components superimposed on the first and second detection signals S1 and S2 is amplified by the differential amplifier circuit 16. Therefore, depending on the magnitude of a difference between the direct-current voltage components, a signal amplitude greater than or equal to an output bound occurs. Therefore, in some cases, a signal waveform is clamped or distortion occurs, and hence, it may be difficult to output a correct signal. However, the first and second coupling capacitors 14 and 15 are provided on the output sides of the first and second amplification units 7 and 8, and hence, it is possible to stably measure the first and second detection signals S1 and S2 without being influenced by the first and second high impedance circuits 4 and 5 or the impedance of the body surface.

Figure 2:
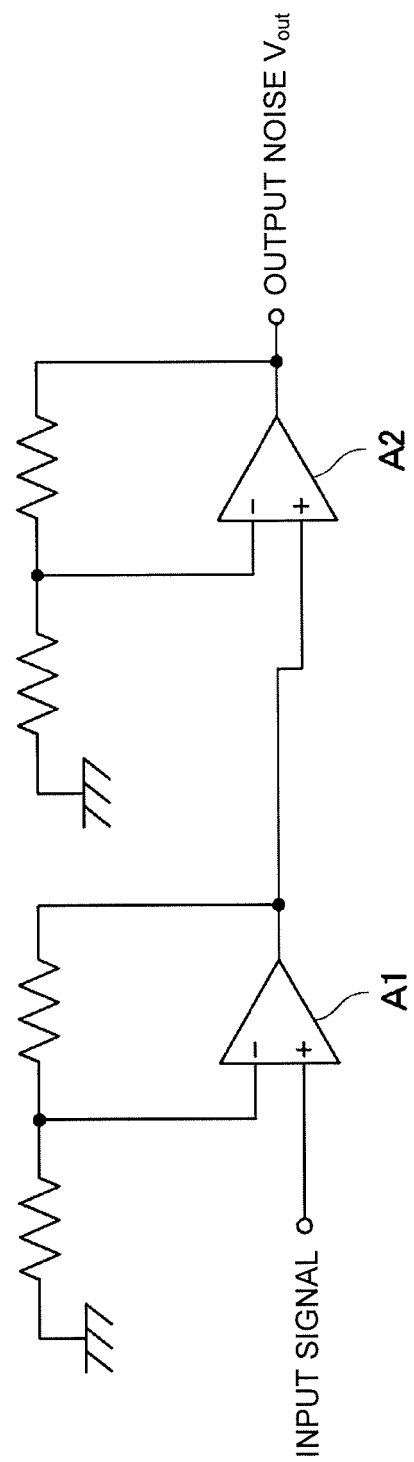
FIG. 2 is an explanatory diagram used for explaining an output noise in total based on an input conversion noise in a two-stage amplifier circuit.

In addition, for example, when a weak signal is detected, a two-stage amplifier circuit is used where a first-stage amplifier $A_1$ having an amplification factor $G_1$ and a subsequent-stage amplifier $A_2$ having an amplification factor $G_2$ are series-connected and two-stage amplification is performed as illustrated in FIG. 2, for example. At this time, if the input conversion noises of the first-stage amplifier $A_1$ and the subsequent-stage amplifier $A_2$ are $V_{n1}$ and $V_{n2}$, respectively, an output noise $V_{out}$ in total, output from the two-stage amplifier circuit, is calculated in accordance with the following Expression 1. In addition, the input conversion noise is a value obtained by dividing, by an amplification factor, a noise level when the input terminal of an amplifier is short-circuited and put into a state in which no external noise is input.

$$V_{out} = V_{n1} \times G_1 \times G_2 + V_{n2} \times G_2 \qquad \text{[Expression 1]}$$
$$= G_1 \times G_2 \left( V_{n1} + \frac{V_{n2}}{G_1} \right)$$

Accordingly, in a case where an amplification factor ($=G_1 \times G_2$) in the two-stage amplifier circuit is set constant and the level allocations of the amplification factors $G_1$ and $G_2$ are compared, when the amplification factor $G_1$ of the first-stage amplifier $A_1$ is set relatively large compared with the amplification factor $G_2$ of the subsequent-stage amplifier $A_2$, $V_{n2}/G_1$ becomes small. Therefore, as a result, it is possible to reduce the output noise $V_{out}$ in the two-stage amplifier circuit. In addition, the same applies to a multi-stage amplifier circuit including three or more amplifiers.

This also applies to the present embodiment. In particular, in the present embodiment, since the coupling capacitors 14 and 15 are disposed at positions between the first and second amplification units 7 and 8 and the differential amplifier circuit 16, it is possible to make the amplification factors of the first and second amplification units 7 and 8 located in a first stage as high as possible and make the amplification degree of the differential amplifier circuit 16 relatively small with respect to the amplification factors of the first and second amplification units 7 and 8. As a result, since it is possible to reduce the output noise in total in the measurement device 1, it is possible to obtain the differentially amplified signal V3 that is desired for detection and correct.

In addition, specifically, the amplification factors of the first and second amplification units 7 and 8 are set high, and the first and second output signals V1 and V2 are caused to be values near to a maximum value of the driving voltage Vdd, within the range of the driving voltage Vdd causing the operational amplifier 17 in the differential amplifier circuit 16 to operate. Therefore, it is possible to improve the SN ratio of the measurement device 1. In addition, since it is possible to set the amplification factor of the differential amplifier circuit 16 low, the differential amplifier circuit 16 removing the direct-current voltage components of the first and second output signals V1 and V2, a common-mode-noise cancelling performance is enhanced, and it is possible to obtain the differentially amplified signal V3 that is desired for detection and correct.

Furthermore, specifically, the amplification factors of the first and second amplification units 7 and 8 are set high within a range lower than the input level of the A/D converter circuit 23 such that the first and second output signals V1 and V2 are caused to be values near to the input level. Therefore, it is possible to improve the SN ratio of the measurement device 1. In addition to this, it is possible to improve the degree of accuracy when being quantized and discretized into a digital signal by the A/D converter circuit 23.

In addition, the arithmetic unit 22 performs arithmetic processing on the basis of the differentially amplified signal V3 output from the differential amplifier circuit 16, and generates biological information such as electrocardiogram data. This biological information is stored in a storage unit, and displayed in a display panel (not illustrated) such as, for example, a liquid crystal display screen.

Figure 3:
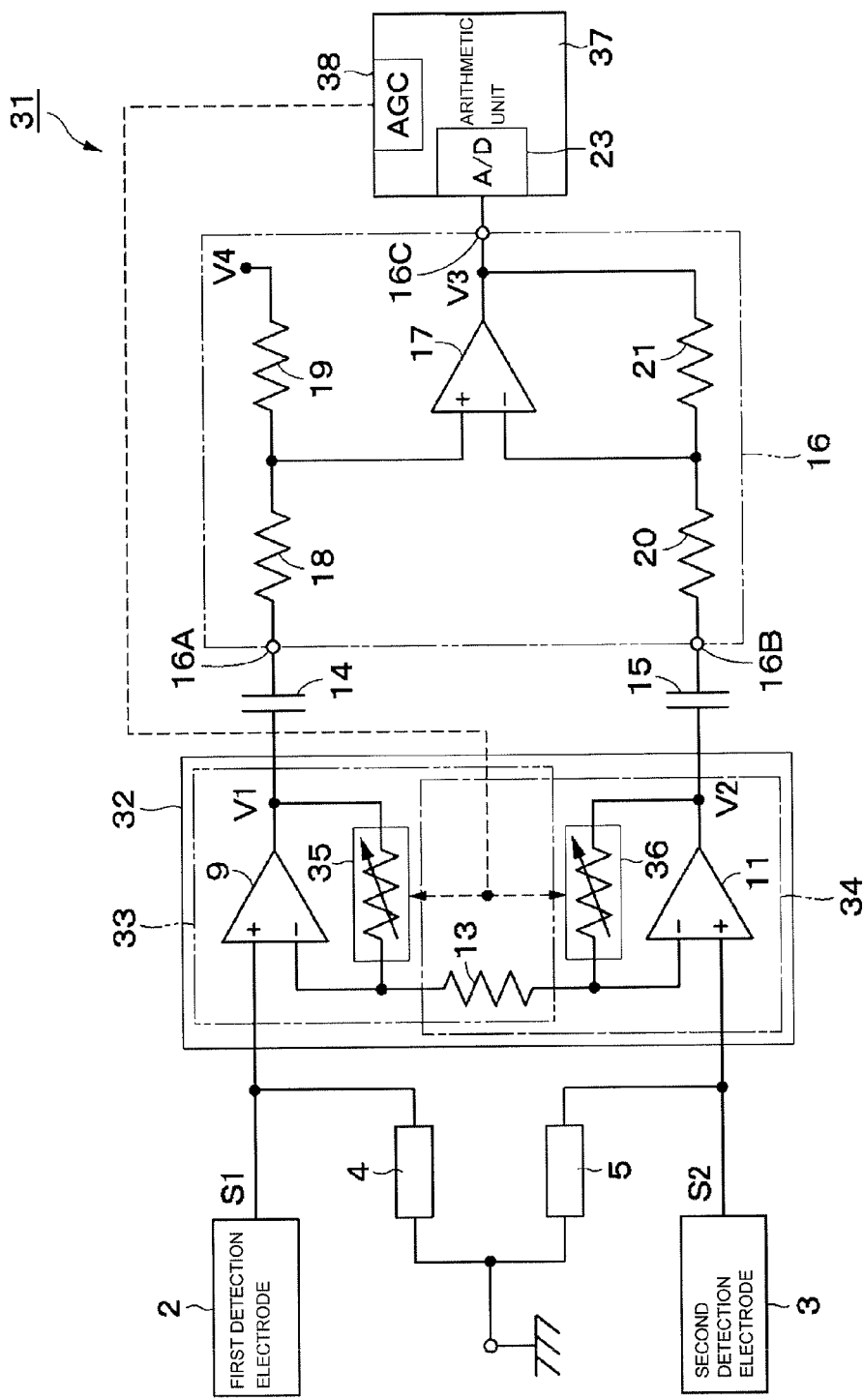
FIG. 3 is a circuit diagram illustrating a measurement device for biological information according to a second embodiment.

Next, a second embodiment of the present invention will be illustrated in FIG. 3. The second embodiment is characterized by a configuration including an automatic gain control circuit controlling the amplification factor of a first amplification unit and the amplification factor of a second amplification unit on the basis of a feedback signal based on a differential signal. In addition, in the second embodiment, the same symbol will be assigned to the same configuration element as in the above-mentioned first embodiment, and the description thereof will be omitted.

In substantially the same way as the measurement device 1 according to the first embodiment, a measurement device 31 includes the first and second detection electrodes 2 and 3, the first and second high impedance circuits 4 and 5, an amplifier circuit 32, the first and second coupling capacitors 14 and 15, the differential amplifier circuit 16, and an arithmetic unit 37.

The amplifier circuit 32 includes a first amplification unit 33 and a second amplification unit 34. The first amplification unit 33 is configured using the operational amplifier 9 (Op-amp), and the output terminal and the inverting terminal of the operational amplifier 9 are connected to each other through a variable resistance element 35 whose resistance value is adjustable. The non-inverting terminal of the operational amplifier 9 is connected to a common connection point between the first detection electrode 2 and the high impedance circuit 4. In substantially the same way as the first amplification unit 33, the second amplification unit 34 is configured using the operational amplifier 11 (Op-amp), and the output terminal and the inverting terminal of the operational amplifier 11 are connected to each other through a variable resistance element 36 whose resistance value is adjustable. The non-inverting terminal of the operational amplifier 11 is connected to a common connection point between the second detection electrode 3 and the high impedance circuit 5. In addition, the inverting terminals of the operational amplifier 9 and the operational amplifier 11 are connected to each other through a resistor 13.

As a result, the first amplification unit 33 configures a non-inverting amplifier circuit using the operational amplifier 9, the resistor 13, and the variable resistance element 35, and amplifies the first detection signal S1 to output the first output signal V1. In addition, the amplification factor thereof depends on the resistance values of the resistor 13 and the variable resistance element 35. In addition, the second amplification unit 34 configures a non-inverting amplifier circuit using the operational amplifier 11, the resistor 13, and the variable resistance element 36, and amplifies the second detection signal S2 to output the second output signal V2. In addition, the amplification factor thereof depends on the resistance values of the resistor 13 and the variable resistance element 36.

The variable resistance elements 35 and 36 are configured using, for example, field-effect transistors. In addition, when a control signal from an AGC circuit 38 provided in the arithmetic unit 37 described later is supplied to a gate, a resistance value between a source and a drain in the field-effect transistor changes.

The arithmetic unit 37 is connected to the output terminal 16C of the operational amplifier 17, and calculates biological information such as an electrocardiogram on the basis of the differentially amplified signal V3. The arithmetic unit 37 includes a microcomputer, and on the input side thereof, the A/D converter circuit 23 is provided.

In addition, the arithmetic unit 37 includes the AGC circuit (automatic gain control circuit) 38. On the basis of a feedback signal based on the differentially amplified signal V3 of the differential amplifier circuit 16, the AGC circuit 38 varies the resistance values of the variable resistance elements 35 and 36, and controls the amplification factors of the first and second amplification units 33 and 34. Specifically, the AGC circuit 38 compares, in magnitude, the amplitude of the differentially amplified signal V3 and a predetermined determination value preliminarily defined with each other, adjusts the resistance values of the variable resistance elements 35 and 36, and varies the amplification factors of the first and second amplification units 33 and 34.

In this way, in the second embodiment, it is also possible to obtain the same function effect as in the first embodiment. In particular, in the second embodiment, owing to the feedback signal based on the differentially amplified signal V3 from the differential amplifier circuit 16, the amplification factors of the first and second amplification units 33 and 34 are controlled by the AGC circuit 38. In this way, in response to the magnitude of the differentially amplified signal V3, it is possible to increase the amplification factors of the first and second amplification units 33 and 34 and reduce noises in the first and second detection signals S1 and S2 as a result.

In addition, the variable resistance elements 35 and 36 are provided in the first and second amplification units 33 and 34, respectively, and the resistance values of the variable resistance elements 35 and 36 are separately controlled by the AGC circuit 38. Therefore, it is possible to vary the amplification factors of the first and second amplification units 33 and 34 independently from each other. Therefore, even if common mode noises whose magnitudes are different are input to the first and second detection electrodes 2 and 3, it is possible to cancel out the noises owing to the differential amplifier circuit 16 after the magnitudes have been caused to coincide with each other by separately controlling the amplification factors of the first and second amplification units 33 and 34.

In addition, while, in the second embodiment, a configuration is adopted where the amplification factors of the first and second amplification units 33 and 34 are controlled by the single AGC circuit 38, AGC circuits may also be provided that control the first and second amplification units 33 and 34 separately.

Figure 4:
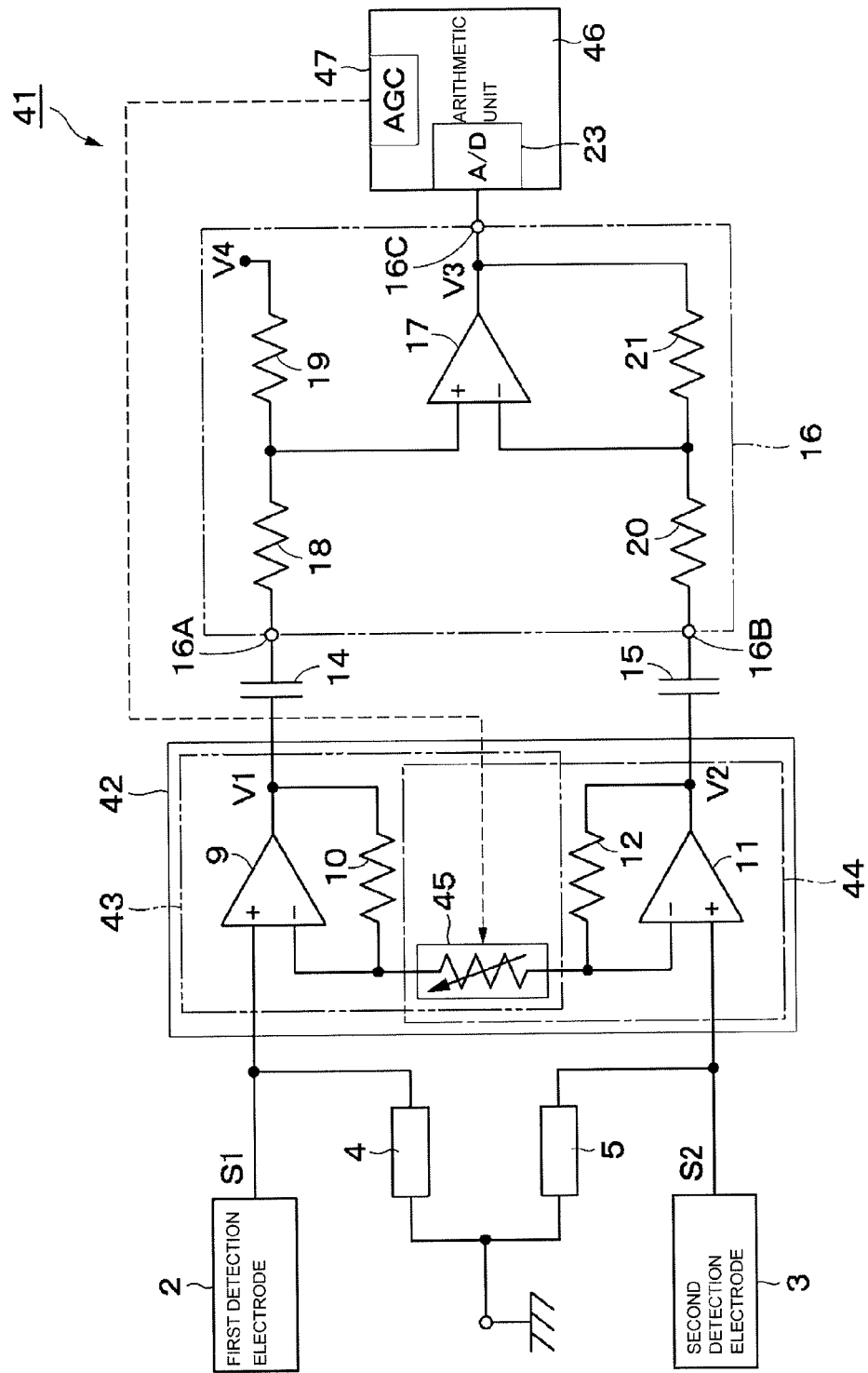
FIG. 4 is a circuit diagram illustrating a measurement device for biological information according to a third embodiment.

Next, a third embodiment of the present invention will be illustrated in FIG. 4. The third embodiment is characterized by a configuration where the resistance value of a single variable resistor is adjusted by an automatic gain control circuit and the amplification factors of first and second amplification units are simultaneously controlled. In addition, in the present embodiment, the same symbol will be assigned to the same configuration element as in the above-mentioned first embodiment, and the description thereof will be omitted.

In substantially the same way as the measurement device 1 according to the first embodiment, a measurement device 41 includes the first and second detection electrodes 2 and 3, the first and second high impedance circuits 4 and 5, an amplifier circuit 42, the first and second coupling capacitors 14 and 15, the differential amplifier circuit 16, and an arithmetic unit 46.

The amplifier circuit 42 includes a first amplification unit 43 and a second amplification unit 44. The first amplification unit 43 is configured using the operational amplifier 9 (Op-amp), and the output terminal and the inverting terminal of the operational amplifier 9 are connected to each other through the resistor 10. The non-inverting terminal of the operational amplifier 9 is connected to a common connection point between the first detection electrode 2 and the high impedance circuit 4. In substantially the same way as the first amplification unit 43, the second amplification unit 44 is configured using the operational amplifier 11 (Op-amp), and the output terminal and the inverting terminal of the operational amplifier 11 are connected to each other through the resistor 12. The non-inverting terminal of the operational amplifier 11 is connected to a common connection point between the second detection electrode 3 and the high impedance circuit 5. In addition, the inverting terminals of the operational amplifier 9 and the operational amplifier 11 are connected to each other through a variable resistance element 45.

As a result, the first amplification unit 43 configures a non-inverting amplifier circuit using the operational amplifier 9, the resistor 10, and the variable resistance element 45, and amplifies the first detection signal S1 to output the first output signal V1. In addition, the amplification factor thereof depends on the resistance values of the resistor 10 and the variable resistance element 45. In addition, the second amplification unit 44 configures a non-inverting amplifier circuit using the operational amplifier 11, the resistor 12, and the variable resistance element 45, and amplifies the second detection signal S2 to output the second output signal V2. In addition, the amplification factor thereof depends on the resistance values of the resistor 12 and the variable resistance element 45.

The arithmetic unit 46 is connected to the output terminal 16C of the operational amplifier 17, and calculates biological information such as an electrocardiogram on the basis of the differentially amplified signal V3. The arithmetic unit 46 includes a microcomputer, and on the input side thereof, the A/D converter circuit 23 is provided. In addition, owing to the A/D converter circuit 23, the arithmetic unit 46 converts the differentially amplified signal V3 including an analog signal into a digital signal, and performs various kinds of arithmetic processing.

In addition, the arithmetic unit 46 includes an AGC circuit (automatic gain control circuit) 47. On the basis of a feedback signal based on the differentially amplified signal V3 of the differential amplifier circuit 16, the AGC circuit 47 varies the resistance value of the variable resistance element 45, and controls the amplification factors of the first and second amplification units 43 and 44. Specifically, the AGC circuit 47 compares, in magnitude, the amplitude of the differentially amplified signal V3 and a predetermined determination value preliminarily defined with each other, adjusts the resistance value of the variable resistance element 45, and varies the amplification factors of the first and second amplification units 43 and 44.

In this way, in the third embodiment, it is also possible to obtain the same function effect as in the first and second embodiments. In particular, in the third embodiment, on the basis of the feedback signal based on the differentially amplified signal V3 from the differential amplifier circuit 16, the AGC circuit 47 varies the resistance value of the variable resistance element 45. As a result, in response to the magnitude of the differentially amplified signal V3, the amplification factors of the first and second amplification units 43 and 44 are simultaneously controlled. In addition, if the resistance values of the resistors 10 and 12 are set to a same value, the amplification factors of the first and second amplification units 43 and 44 become equal to each other. Accordingly, distortion hardly occurs in the first and second output signals V1 and V2 input to the differential amplifier circuit 16.

Furthermore, since the resistance value of the single variable resistance element 45 is varied and the amplification factors of the first and second amplification units 43 and 44 are simultaneously controlled, it becomes easy to perform control and the configuration is simplified, compared with the second embodiment.

In addition, while, in the second and third embodiments, a configuration is exemplified where field-effect transistors are only used as the variable resistance elements 35, 36, and 45, a configuration may also be adopted where a fixed resistance element is connected in parallel between the drain and source of the field-effect transistor and a steep change in resistance is reduced.

In addition, a configuration may also be adopted where bipolar transistors or diodes are used as the variable resistance elements 35, 36, and 45, and a configuration may also be adopted where a potentiometer, a digital potentiometer, or the like is used.

Figure 5:
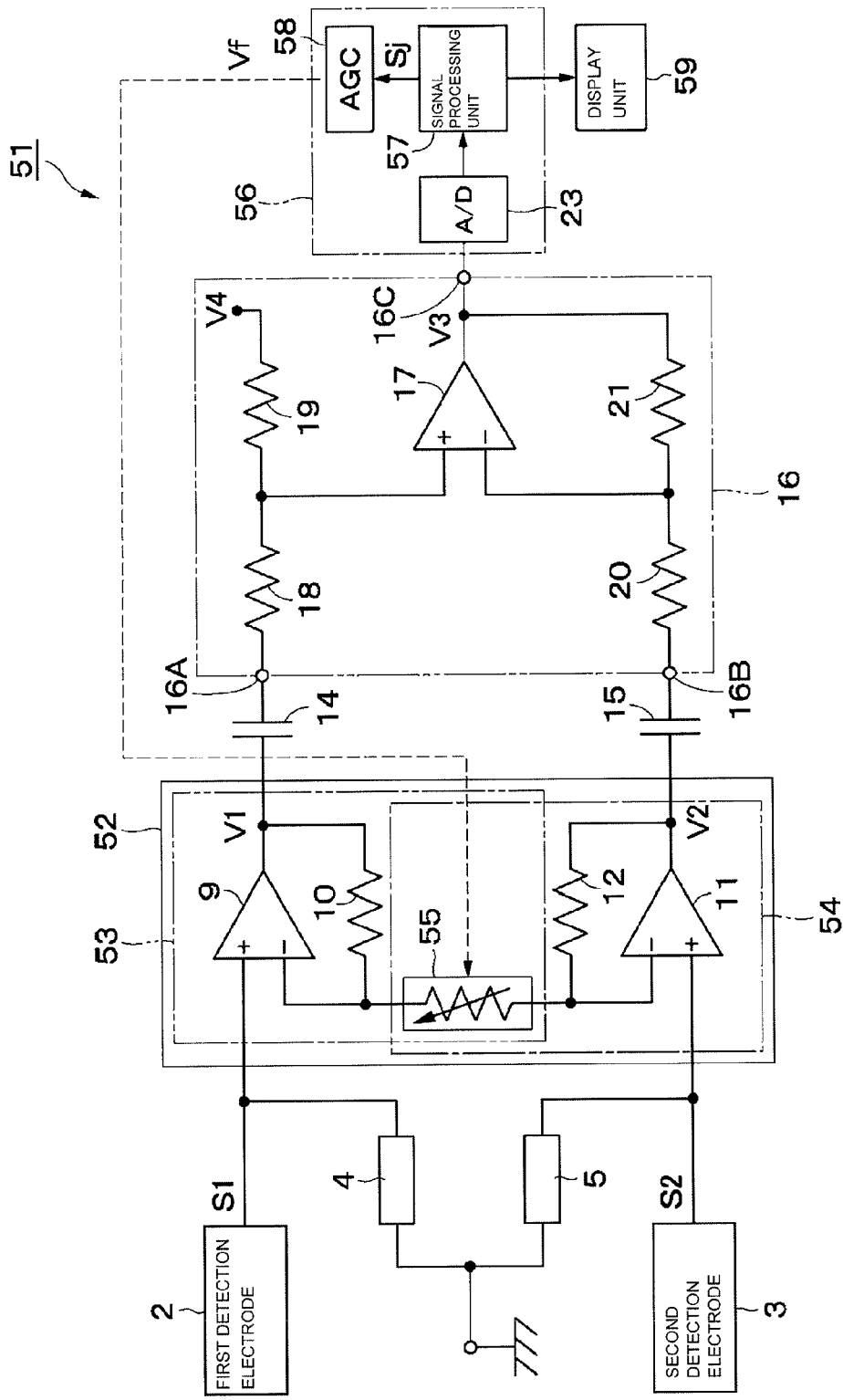
FIG. 5 is a circuit diagram illustrating a measurement device for biological information according to a fourth embodiment.

Next, a fourth embodiment of the present invention will be illustrated in FIG. 5. The fourth embodiment is characterized by a configuration where an automatic gain control circuit controls the amplification factors of first and second amplification units in response to a difference between the peak value of a differentially amplified signal and a baseline value. In addition, in the present embodiment, the same symbol will be assigned to the same configuration element as in the above-mentioned first embodiment, and the description thereof will be omitted.

In substantially the same way as the measurement device 1 according to the first embodiment, a measurement device 51 includes the first and second detection electrodes 2 and 3, the first and second high impedance circuits 4 and 5, an amplifier circuit 52, the first and second coupling capacitors 14 and 15, the differential amplifier circuit 16, and an arithmetic unit 56.

When the measurement device 51 is used for the measurement of biological information, the first and second detection electrodes 2 and 3 are caused to be in contact with predetermined positions in a living body such as a person or an animal, and temporal changes in the action potentials of a heart changing in association with the beat of the heart of the living body are detected as the first and second detection signals S1 and S2. At this time, the differential amplifier circuit 16 outputs, to the arithmetic unit 56, the differentially amplified signal V3 corresponding to a difference between the first and second detection signals S1 and S2 as a heartbeat signal serving as a living body signal.

Figure 6:
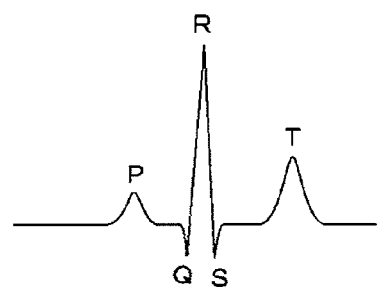
FIG. 6 is a diagram illustrating a typical normal waveform of a heartbeat signal.

Here, a typical normal waveform corresponding to one heartbeat of the heartbeat signal is illustrated in FIG. 6. This heartbeat signal waveform includes five waves containing a P wave, a Q wave, an R wave, an S wave, and a T wave and a U wave not illustrated. The Q wave, the R wave, and the S wave are collectively called a QRS wave. The P wave is the wave of an action potential occurring owing to atrial activation, the QRS wave is the wave of an action potential occurring owing to ventricular activation, and the T wave is the wave of an action potential occurring in a process in which the myocardial cells of the activated ventricle are repolarized.

An amplifier circuit 52 is configured in substantially the same way as the amplifier circuit 42 according to the third embodiment, and includes a first amplification unit 53 including the operational amplifier 9 and so forth and a second amplification unit 54 including the operational amplifier 11 and so forth. In addition, the inverting terminals of the operational amplifier 9 and the operational amplifier 11 are connected to each other through a variable resistance element 55. Furthermore, the output terminal of the first amplification unit 53 is connected to the first input terminal 16A of the differential amplifier circuit 16 through the first coupling capacitor 14, and the output terminal of the second amplification unit 54 is connected to the second input terminal 16B of the differential amplifier circuit 16 through the second coupling capacitor 15.

In addition, the first amplification unit 53 configures a non-inverting amplifier circuit using the operational amplifier 9, the resistor 10, and the variable resistance element 55, and amplifies the first detection signal S1 to output the first output signal V1. In addition, the amplification factor thereof depends on the resistance values of the resistor 10 and the variable resistance element 55. In addition, the second amplification unit 54 configures a non-inverting amplifier circuit using the operational amplifier 11, the resistor 12, and the variable resistance element 55, and amplifies the second detection signal S2 to output the second output signal V2. In addition, the amplification factor thereof depends on the resistance values of the resistor 12 and the variable resistance element 55.

The arithmetic unit 56 configures a digital processing circuit, is connected to the output terminal 16C of the differential amplifier circuit 16, and calculates biological information such as an electrocardiographic waveform and the number of pulses (the number of heartbeats) on the basis of the differentially amplified signal V3. The arithmetic unit 56 includes the A/D converter circuit 23 converting the differentially amplified signal V3 including an analog signal into a digital signal, a signal processing unit 57 performing after-mentioned arithmetic processing on the digital signal, and an AGC circuit (automatic gain control circuit) 58 controlling the amplification factors of the first and second amplification units 53 and 54 in response to a determination signal Sj output from the signal processing unit 57.

Here, the signal processing unit 57 is configured using a microcomputer or the like including a CPU (central processing unit), a ROM (read-only memory), and a RAM (readable and writable memory). In accordance with a number-of-pulses calculation program stored in the ROM, the CPU performs predetermined arithmetic processing with the RAM as a temporary storage work area, and calculates the number of pulses. The calculated number of pulses is displayed in a display unit 59 including an LCD (liquid crystal display device), organic EL (electroluminescence), or the like.

In addition, the signal processing unit 57 calculates a difference D between the peak value P of the differentially amplified signal V3 and a baseline value G serving as a reference value, and compares the difference D with a predetermined first threshold value D1 and a second threshold value D2, preliminarily defined, to output the determination signal Sj. The AGC circuit 58 outputs a feedback signal Vf according to this determination signal Sj, and varies the resistance value of the variable resistance element 55. In this way, in response to the difference D between the peak value P of the differentially amplified signal V3 and the baseline value G, the AGC circuit 58 varies the amplification factors of the first and second amplification units 53 and 54.

Owing to the number-of-pulses calculation program stored in the ROM, the CPU in the signal processing unit 57 functions as a maximum value detection means, a determination time reset means, a peak value determination means, a pulse calculation means, a sequential change means, and a comparison means.

The maximum value detection means acquires the differentially amplified signal V3 that serves as a heartbeat signal and is output from the differential amplifier circuit 16 at a predetermined sampling time interval, and detects the maximum value M of the heartbeat signal. In the present embodiment, the heartbeat signal is acquired at, for example, the sampling time interval of 600 [Hz], and the maximum value M of the detected heartbeat signal is stored in the RAM by the CPU.

When no new maximum value M1 larger than the maximum value M detected by the maximum value detection means is detected by the maximum value detection means within a given determination time T1, the peak value determination means determines that the maximum value M detected by the maximum value detection means is a peak value P. For example, when a series of heartbeat signals illustrated in FIG. 7 have been acquired by the signal processing unit 57 and no maximum value M1 larger than the maximum value M is detected by the maximum value detection means within the determination time T1, the maximum value M being detected by the maximum value detection means at a time t1 and corresponding to the R wave of a heartbeat signal Sa, the peak value determination means determines that the maximum value M detected by the maximum value detection means at the time t1 is the peak value P. A time t2 when the determination time T1 has elapsed from the time t1 and when the peak value P is determined by the peak value determination means is defined as a peak determination point tp. The peak value P determined by the peak value determination means is stored in the RAM. Here, the magnitude of each heartbeat signal in the series of heartbeat signals fluctuates with the baseline value G as a reference, the baseline value G serving as the central potentials of the first and second detection signals S1 and S2. In addition, the determination time T1 is a time during which the maximum value M detected by the maximum value detection means is not updated, and timed by being counted by a maximum value update counter formed in a predetermined region in the RAM.

When a new maximum value M1 larger than the maximum value M detected by the maximum value detection means has been detected by the maximum value detection means within the determination time T1, the determination time reset means updates the maximum value M to the new maximum value M1, resets the maximum value update counter timing the determination time T1, and times again the determination time T1 from a time point when the new maximum value M1 has been detected.

Figure 7:
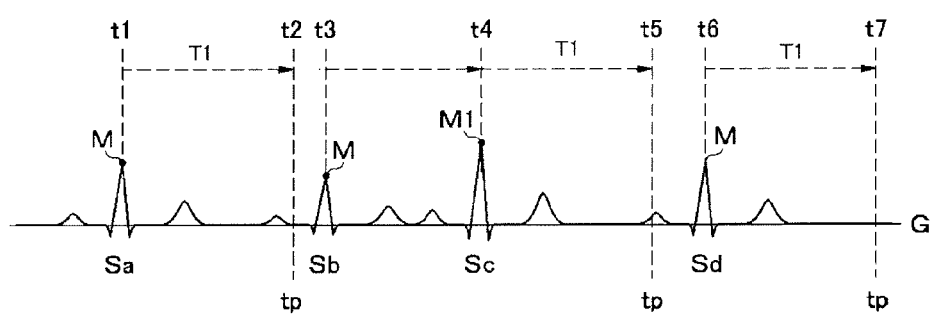
FIG. 7 is an explanatory diagram illustrating a series of heartbeat signals used for explaining peak value determination performed in a signal processing unit in the measurement device in FIG. 5.

Therefore, when no new maximum value M2 even larger than the large maximum value M1 is detected by the maximum value detection means within the determination time T1 from the time point when the large maximum value M1 had been detected, the peak value determination means determines that the large maximum value M1 detected by the maximum value detection means is the peak value P. For example, as illustrated in FIG. 7, in a case where the maximum value M1 of a heartbeat signal Sc even larger than the maximum value M of a heartbeat signal Sb detected by the maximum value detection means at a time t3 has been detected by the maximum value detection means at a time t4 within the determination time T1 from the time t3, when no maximum value M2 even larger than the large maximum value M1 is detected by the maximum value detection means within the determination time T1 from the time t4 when the large maximum value M1 has been detected, the large maximum value M1 detected by the maximum value detection means is determined as the peak value P, at a peak determination point tp at a time t5 when the determination time T1 has elapsed from the time t4. In addition, the determined peak value P is stored in the RAM.

After that, in the same way, when no maximum value M1 larger than the maximum value M of a heartbeat signal Sd detected by the maximum value detection means at a time t6 is detected by the maximum value detection means within the determination time T1, the peak value determination means determines the maximum value M detected by the maximum value detection means at the time t6, as the peak value P, at a peak determination point tp at a time t7 when the determination time T1 has elapsed from the time t6, and stores the maximum value M in the RAM.

On the basis of a time interval T2 between the successive peak values P determined by the peak value determination means, the pulse calculation means obtains the number of the peak values P occurring per minute, and calculates the rhythmic period of the beat of the living body causing a living body signal to occur, as the number of pulses. For example, as illustrated in a series of heartbeat signals in FIG. 8, the time interval T2 between the successive peak values P is a time interval between a time t8 when the maximum value M of a heartbeat signal Se has been detected that has been determined as the peak value P and stored in the RAM and a time t9 when the maximum value M of a heartbeat signal Sf has been detected that has been determined as the peak value P and stored in the RAM. In the same way, the time interval T2 between the successive peak values P is a time interval between the time t9 when the maximum value M of the heartbeat signal Sf has been detected that has been determined as the peak value P and stored in the RAM and a time t10 when the maximum value M of a heartbeat signal Sg has been detected that has been determined as the peak value P and stored in the RAM. In addition, in FIG. 8, the same symbol is assigned to the same as in FIG. 7, and the description thereof will be omitted. This time interval T2 between the successive peak values P is counted by a peak interval counter formed in a predetermined region in the RAM separately from the maximum value update counter timing the determination time T1 during which the maximum value M is not updated, and hence, the time interval T2 between the successive peak values P is timed.

When the initial maximum value M has been determined as the peak value P at the peak determination point tp immediately after the determination time T1 has elapsed and the maximum value M occurring immediately after that peak determination point tp is determined as the peak value P at the subsequent peak determination point tp immediately after the determination time T1 has further elapsed, the time interval T2 between the peak values P becomes a minimum time interval, and becomes a time interval slightly exceeding the determination time T1. In addition, when the initial maximum value M has been determined as the peak value P at the peak determination point tp immediately after the determination time T1 has elapsed and the maximum value M occurring immediately before the determination time T1 has elapsed from that peak determination point tp is determined as the peak value P at the subsequent peak determination point tp immediately after the determination time T1 has elapsed from that peak determination point tp, the time interval T2 between the peak values P becomes a maximum time interval, and becomes a time interval slightly falling below twice as long as the determination time T1. Since the standard value of the number of pulses of an adult is 60 to 90 per minute, by setting the determination time T1 to 0.5 [s (second)], the time interval T2 between the peak values P, whose minimum slightly exceeds 0.5 [s] and whose maximum falls below 1 [s] corresponding to twice as long as 0.5 [s], is measured, and the number of pulses greater than 60 (=60÷1) and less than 120 (=60÷0.5) is measured. However, this only enables to measure the standard number of pulses of an adult.

Therefore, in response to the time interval T2 between the successive peak values P, determined by the peak value determination means, the sequential change means sequentially changes the determination time T1 to one period of time from among a plurality of periods of time preliminarily defined in response to the time interval T2 between the peak values P.

In the present embodiment, when determination times T1 of 0.3 [s], 0.4 [s], 0.5 [s], and 0.75 [s] are preliminarily defined with being associated with the time intervals T2 between the successive peak values P, greater than 0.3 [s] and less than 0.5 [s], greater than 0.5 [s] and less than 0.6 [s], greater than 0.6 [s] and less than 0.8 [s], and greater than 0.8 [s], respectively. In this way, the determination time T1 is caused to continually fluctuate to an optimum time from among the plural four times containing 0.3 [s], 0.4 [s], 0.5 [s], and 0.75 [s]. When the determination time T1 is defined as 0.3 [s], the range of the number of pulses greater than 100 (=60÷0.6) and less than 200 (=60÷0.3) is measured. When the determination time T1 is defined as 0.4 [s], the range of the number of pulses greater than 75 (=60÷0.8) and less than 150 (=60÷0.4) is measured. When the determination time T1 is defined as 0.5 [s], the range of the number of pulses greater than 60 (=60÷1.0) and less than 120 (=60÷0.5) is measured. When the determination time T1 is defined as 0.75 [s], the range of the number of pulses greater than 40 (=60÷1.5) and less than 80 (=60÷0.75) is measured. As a result, the number of pulses greater than 40 and less than 200 turns out to be measured, and it is possible to measure the numbers of pulses of wide categories such as a person, an animal, and so forth without being limited to the standard number of pulses of an adult.

Figure 8:
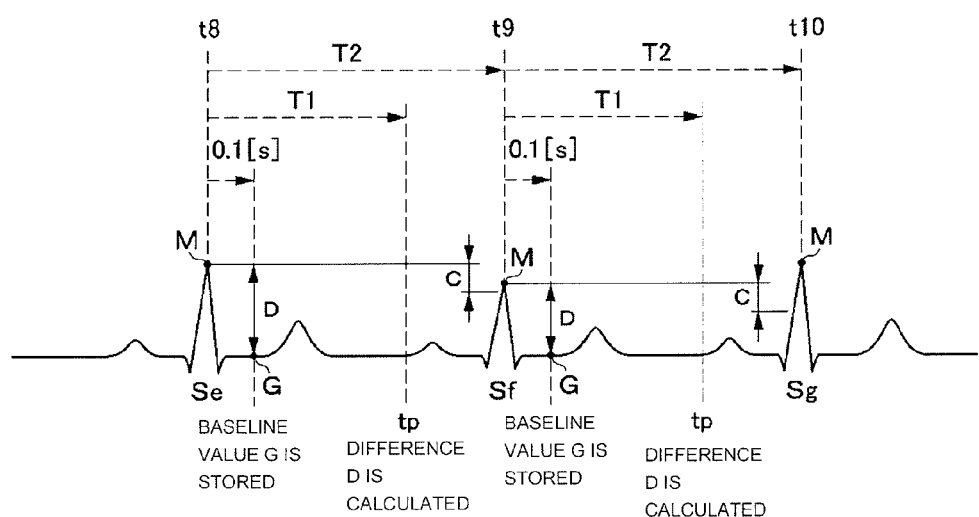
FIG. 8 is an explanatory diagram illustrating a series of heartbeat signals used for explaining a time interval between successive peak values, calculated in the signal processing unit in the measurement device in FIG. 5.

In addition, in the present embodiment, in response to the time interval T2 between the successive peak values P whose mutual values fall within a predetermined range, determined by the peak value determination means, the sequential change means sequentially changes the determination time T1. For example, as illustrated in FIG. 8, when the peak value P of the heartbeat signal Sf has the maximum value M greater than or equal to a value obtained by subtracting a given value C from the maximum value M defined as the peak value P of the heartbeat signal Se, the mutual values of the successive peak values P of the heartbeat signal Se and the heartbeat signal Sf are determined to fall within the predetermined range, by the sequential change means. In the same way, when the peak value P of the heartbeat signal Sg has the maximum value M greater than or equal to a value obtained by subtracting the given value C from the maximum value M defined as the peak value P of the heartbeat signal Sf, the mutual values of the successive peak values P of the heartbeat signal Sf and the heartbeat signal Sg are determined to fall within the predetermined range, by the sequential change means. In response to the time interval T2 between the peak values P whose mutual values have been determined to fall within the predetermined range in this way, the determination time T1 is sequentially changed by the sequential change means.

The comparison means obtains the difference D between the peak value P obtained by the peak value determination means and the baseline value G, and compares the difference D with, for example, a first threshold value D1 and a second threshold value D2, preliminarily set. In the case of a normally functioning heartbeat signal, it has been known that an ST segment from the S wave to the T wave serves as a baseline, and is stable with respect to, for example, a ground potential serving as a reference measurement electric potential. Therefore, in the present embodiment, so as to obtain an input value in the ST segment, the input value of the differentially amplified signal V3 at a time point when 0.1 [s] has elapsed from the maximum value M corresponding to the R wave of the heartbeat signal is stored, as the baseline value G, in the RAM.

In addition, when the determination time T1 has elapsed and the peak value P has been confirmed, the comparison means calculates the difference D between the peak value P and the baseline value G. In addition, a case may be considered where the plus and minus of the waveform of the heartbeat signal are inverted according to the differentially amplified signal V3 and the peak value P has a negative value. In view of this point, the difference D between the peak value P and the baseline value G may also be calculated as an absolute value.

In addition, the first threshold value D1 indicates a lower limit value where when the difference D becomes smaller than or equal to the first threshold value D1, for example the SN ratio is reduced, the R wave becomes buried in a noise, and it becomes difficult to detect the peak value P. On the other hand, the second threshold value D2 indicates an upper limit value where when the difference D becomes greater than or equal to the second threshold value D2, for example the R wave exceeds the resolution capability of the A/D converter circuit 23 to become excessive and it becomes difficult to detect the peak value P. Therefore, the second threshold value D2 is a value greater than the first threshold value D1, and these threshold values D1 and D2 are preliminarily set.

In addition, when the difference D between the peak value P and the baseline value G has become less than or equal to the first threshold value D1, for example, four times in a row as the predetermined number of times preliminarily defined, the comparison means outputs the determination signal Sj of a Low state indicating that the difference D is excessively small. On the other hand, when the difference D between the peak value P and the baseline value G has become greater than or equal to the second threshold value D2, for example, four times in a row as the predetermined number of times preliminarily defined, the comparison means outputs the determination signal Sj of a High state indicating that the difference D is excessive. When a same comparison result has not occurred a predetermined number of times in a row or when the difference D between the peak value P and the baseline value G is located between the first threshold value D1 and the second threshold value D2, the comparison means outputs the previous determination signal Sj without change.

In this way, when the determination signal Sj of a High state has been output from the signal processing unit 57, the AGC circuit 58 outputs the feedback signal Vf causing the amplification factors of the first and second amplification units 53 and 54 to be decreased. On the other hand, when the determination signal Sj of a Low state has been output from the signal processing unit 57, the AGC circuit 58 outputs the feedback signal Vf causing the amplification factors of the first and second amplification units 53 and 54 to be increased.

In addition, the reason that it is confirmed whether or not a same comparison result has occurred a predetermined number of times in a row is that changes in the amplification factors of the first and second amplification units 53 and 54 are prevented from being frequently switched more than necessary. Accordingly, the predetermined number of times may also be set to two, three, or a value greater than or equal to five, and may also be set to one if the amplification factors are allowed to be switched every time.

Next, with reference to flowcharts in FIG. 10 and FIG. 11, processing for calculating the number of pulses will be described that is performed by the CPU in accordance with the above-mentioned number-of-pulses calculation program, in the signal processing unit 57 in the measurement device 51 according to the present embodiment.

Figure 10:
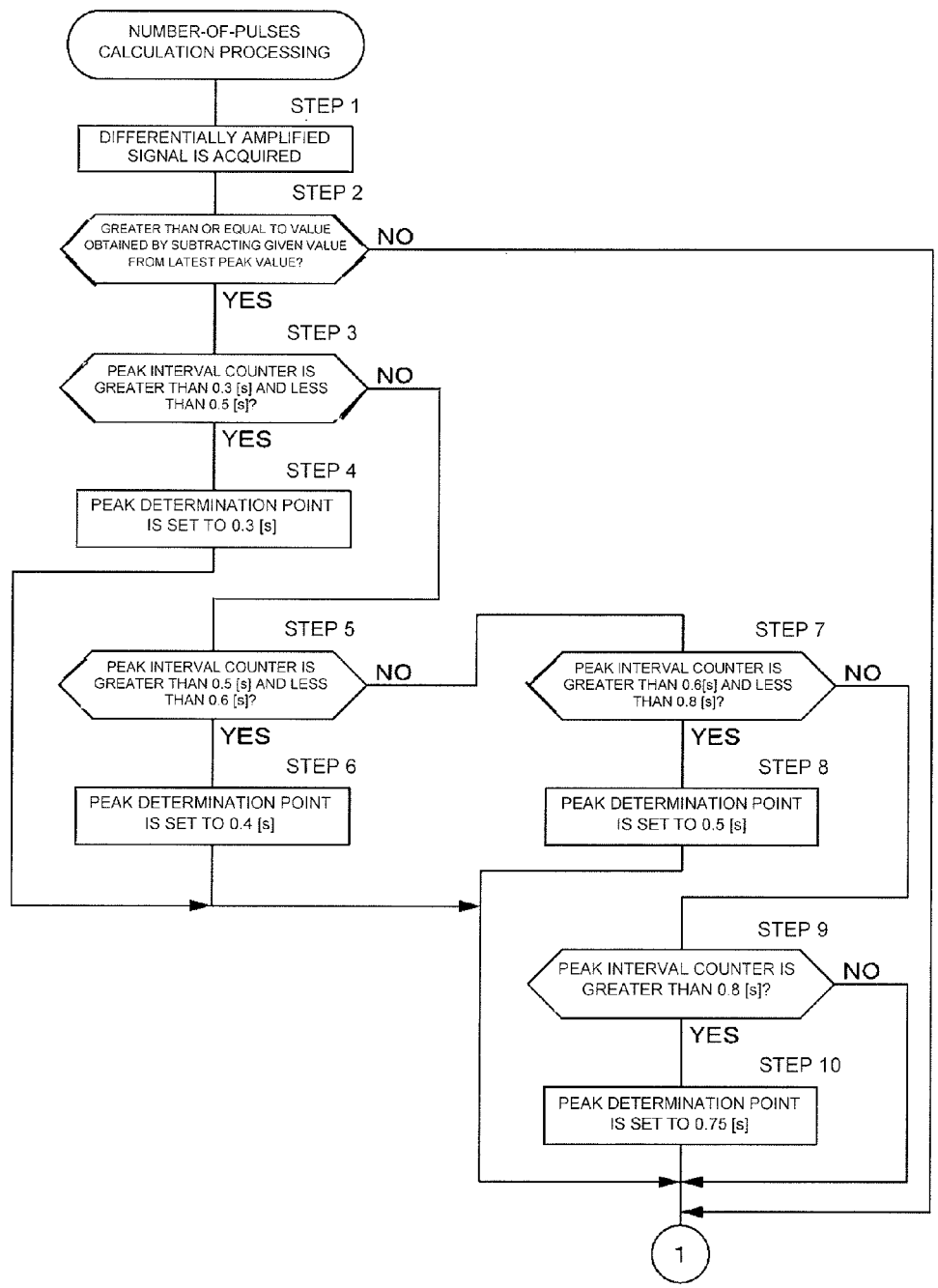
FIGS. 10 and 11 illustrate a flowchart for calculating the number of pulses, performed by the measurement device in FIG. 5.

First, in a step 1 in FIG. 10, the CPU acquires, as a heartbeat signal, the differentially amplified signal V3 at a predetermined sampling time interval, the differentially amplified signal V3 being output from the differential amplifier circuit 16 and converted into a digital signal by the A/D converter circuit 23. In addition, the maximum value M with respect to each of successive sampling times in the heartbeat signal is sequentially detected.

Next, in a step 2, the CPU judges whether or not the maximum value M of the heartbeat signal, acquired at the predetermined sampling time interval, is greater than or equal to a value obtained by subtracting the given value C from the latest peak value P stored in the RAM. When the acquired maximum value M of the heartbeat signal is greater than or equal to the value obtained by subtracting the given value C from the latest peak value P and the judgment result of the step 2 is "YES", in a step 3 the CPU judges whether or not the time interval T2 between the peak values P, counted by the peak interval counter, is greater than 0.3 [s] and less than 0.5 [s].

When the time interval T2 between the peak values P is greater than 0.3 [s] and less than 0.5 [s] and the judgment result of the step 3 is "YES", in a step 4 the CPU sets the determination time T1 to 0.3 [s]. On the other hand, when the time interval T2 between the peak values P is not greater than 0.3 [s] or less than 0.5 [s] and the judgment result of the step 3 is "NO", in a step 5 the CPU judges whether or not the time interval T2 between the peak values P, counted by the peak interval counter, is greater than 0.5 [s] and less than 0.6 [s].

When the time interval T2 between the peak values P is greater than 0.5 [s] and less than 0.6 [s] and the judgment result of the step 5 is "YES", in a step 6 the CPU sets the determination time T1 to 0.4 [s]. On the other hand, when the time interval T2 between the peak values P is not greater than 0.5 [s] or less than 0.6 [s] and the judgment result of the step 5 is "NO", in a step 7 the CPU judges whether or not the time interval T2 between the peak values P, counted by the peak interval counter, is greater than 0.6 [s] and less than 0.8 [s].

When the time interval T2 between the peak values P is greater than 0.6 [s] and less than 0.8 [s] and the judgment result of the step 7 is "YES", in a step 8 the CPU sets the determination time T1 to 0.5 [s]. On the other hand, when the time interval T2 between the peak values P is not greater than 0.6 [s] or less than 0.8 [s] and the judgment result of the step 7 is "NO", in a step 9 the CPU judges whether or not the time interval T2 between the peak values P, counted by the peak interval counter, is greater than 0.8 [s].

When the time interval T2 between the peak values P is greater than 0.8 [s] and the judgment result of the step 9 is "YES", in a step 10 the CPU sets the determination time T1 to 0.75 [s].

When the time interval T2 between the peak values P is not greater than 0.8 [s] and the judgment result of the step 9 is "NO", when the acquired maximum value M of the heartbeat signal is not greater than or equal to the value obtained by subtracting the given value C from the latest peak value P and the judgment result of the step 2 is "NO", or alternatively, when the determination time T1 has been set in the step 4, 6, 8, or 10, next in a step 11 the CPU judges whether or not the maximum value M of the heartbeat signal, acquired in the step 1, is larger than the current maximum value M stored in the RAM.

When the maximum value M of the heartbeat signal, acquired in the step 1, is larger than the current maximum value M of the heartbeat signal Sb, stored in the RAM, as the maximum value M1 of the heartbeat signal Sc illustrated in FIG. 7 and the judgment result of the step 11 is "YES", in a step 12 the CPU rewrites and updates the current maximum value M stored in the RAM, to the maximum value M of the heartbeat signal, acquired in the step 1. In addition, the maximum value update counter counting the determination time T1 and the peak interval counter counting the time interval T2 between the peak values P are reset, and timing due to each counter is resumed.

In addition, when the maximum value M of the heartbeat signal, acquired in the step 1, is not larger than the current maximum value M and the judgment result of the step 11 is "NO", in a step 13 the CPU counts up the individual count values of the maximum value update counter and the peak interval counter, and advances timing.

Next, in a step 14, the CPU judges whether or not the maximum value update counter has become 0.1 [s]. When the maximum value update counter has become 0.1 [s] and the judgment result of the step 14 is "YES", in a step 15 the CPU stores, as the baseline value G, the input value of the heartbeat signal input at this time point, in the RAM.

On the other hand, when the maximum value update counter is smaller than 0.1 [s] or larger than 0.1 [s] and the judgment result of the step 14 is "NO", in a step 16 the CPU judges whether or not a time timed by the maximum value update counter is greater than the determination time T1 serving as the peak determination point tp. When the time timed by the maximum value update counter is greater than the determination time T1 and the judgment result of the step 16 is "YES", in a step 17 the CPU calculates the difference D between the peak value P and the baseline value G.

Next, in a step 18, the CPU judges whether or not the difference D between the peak value P and the baseline value G is less than or equal to the first threshold value D1. When the difference D is less than or equal to the first threshold value D1 and the judgment result of the step 18 is "YES", in a step 19 the CPU judges whether or not a state where the difference D becomes less than or equal to the first threshold value D1 has occurred four times in a row. When the judgment result of the step 19 is "YES", in a step 20 the CPU sets the determination signal Sj to the High state.

On the other hand, when the difference D is greater than the first threshold value D1 and the judgment result of the step 18 is "NO", in a step 21 the CPU judges whether or not the difference D between the peak value P and the baseline value G is greater than or equal to the second threshold value D2. When the difference D is greater than or equal to the second threshold value D2 and the judgment result of the step 21 is "YES", in a step 22 the CPU judges whether or not a state where the difference D becomes greater than or equal to the second threshold value D2 has occurred four times in a row. When the judgment result of the step 22 is "YES", in a step 23 the CPU sets the determination signal Sj to the Low state.

When a same state has not occurred four times in a row and the judgment result of the step 19 or 22 is "NO" or after the processing operation in the step 20 or 23 has been completed, in a step 24 the CPU determines, as the peak value P, the maximum value M of the heartbeat signal, acquired in the step 1, and stores to set, as the latest peak value P, the maximum value M of the heartbeat signal in the RAM. In addition, from the time interval T2 between this latest peak value P and the peak value P having occurred immediately before the latest peak value P, the number of the peak values P per minute is obtained, and the number of pulses is calculated. Subsequently, the maximum value update counter is reset and the maximum value M, stored in the RAM and determined as the current peak value P, is reset.

When the maximum value update counter is not greater than the determination time T1 and the judgment result of the step 16 is "NO" or after the processing operation in the step 12, 15, or 24 has been completed, the CPU returns to the processing operation in the step 1 and repeatedly performs the above-mentioned individual processing operations.

In this way, in the fourth embodiment, it is also possible to obtain the same function effect as in the first and third embodiments. In particular, in the fourth embodiment, on the basis of the feedback signal Vf based on the differentially amplified signal V3, the amplification factors of the first and second amplification units 53 and 54 are controlled by the AGC circuit 58.

In addition, the configuration is adopted where the output terminal 16C of the differential amplifier circuit 16 is connected to the arithmetic unit 56 including the A/D converter circuit 23, the signal processing unit 57, and the AGC circuit 58 and the signal processing unit 57 functions as the maximum value detection means, the determination time reset means, the peak value determination means, and the comparison means.

Here, when the maximum value M of the heartbeat signal acquired at the predetermined sampling time interval has been detected by the maximum value detection means, and in the processing operations in the step 11 and the step 16, the maximum value M larger than the detected maximum value M is not detected by the maximum value detection means within the determination time T1, the maximum value M detected by the maximum value detection means is determined as the peak value P by the peak value determination means, in the processing operation in the step 24. In addition, on the basis of the time interval T2 between the successive peak values P determined by the peak value determination means, the number of pulses is calculated by the pulse calculation means.

Therefore, even if the level of the heartbeat signal is low, as long as the maximum value M of the heartbeat signal detected by the maximum value detection means has a signal level that does not become buried in a noise, it is possible for the measurement device 51 according to the present embodiment to perform the determination of the peak value P and calculate the number of pulses even if the P wave or the T wave (refer to FIG. 6) of the heartbeat signal becomes buried in a noise. In addition, even if the baseline value G (refer to FIG. 7) serving as the reference value of the amplitude of the heartbeat signal fluctuates, as long as, in the same way, the maximum value M of the heartbeat signal detected by the maximum value detection means has a signal level that does not become buried in a noise, it is possible to perform the determination of the peak value P and calculate the number of pulses.

In addition, in response to the time interval T2 between the successive peak values P determined by the peak value determination means, in the processing operations in the steps 3 to 10 the sequential change means sequentially changes the determination time T1 used for the determination of the peak value P to one period of time from among a plurality of periods of time containing 0.3 [s], 0.4 [s], 0.5 [s], and 0.75 [s], preliminarily defined in response to the time interval T2 between the peak values P. Therefore, for example, even if the differentially amplified signal V3 is detected where the period of the peak value P fluctuates as the rhythmic period of the beat of the living body, which sequentially fluctuates, it is possible to prevent the determination time T1 from extending over a plurality of periods, by sequentially changing the determination time T1 in response to the fluctuation of the period, and it is possible to reliably determine the peak value P.

In addition to this, unlike a device in which the determination of the peak value P is performed using complicated arithmetic processing such as division, the determination of the peak value P is performed owing to the simplified arithmetic processing including the processing operation in the step 11 where the magnitude of the acquired heartbeat signal is simply compared, the processing operation in the step 13 where the determination time T1 and the time interval T2 between the peak values P are counted, and the processing operations in the steps 3 to 10 where one period of time from among a plurality of periods of time preliminarily defined is selected in response to the time interval T2 between the peak values P. As a result, the number of pulses sequentially fluctuating is adequately calculated as needed, owing to the simplified arithmetic processing, and it is possible to achieve the miniaturization of the measurement device 51 and reduce the cost thereof.

In addition, according to the measurement device 51 according to the present embodiment, for example, in the processing operation in the step 11, as the heartbeat signal Sc illustrated in FIG. 7, when the maximum value M1 larger than the maximum value M of the heartbeat signal Sb detected by the maximum value detection means has been detected by the maximum value detection means within the determination time T1 from the time t3, the maximum value M is updated to the new maximum value M1 by the determination time reset means in the processing operation in the step 12, and the maximum value update counter and the peak interval counter are reset. In this way, the count of the determination time T1 is resumed from the time t4 at a time point when the large maximum value M1 has been detected. In addition, when, in the subsequent processing operations in the step 11 and step 16, the maximum value M2 even larger than the large maximum value M1 is not detected by the maximum value detection means during this determination time T1, the large maximum value M1 detected by the maximum value detection means is determined as the peak value P by the peak value determination means, in the processing operation in the step 24.

Therefore, the maximum value M detected once by the maximum value detection means is removed from data used for calculating the number of pulses without being used for peak determination when the maximum value M1 larger than that maximum value M has been detected by the maximum value detection means within the determination time T1. As a result, from among the maximum values M detected by the maximum value detection means, the maximum value M that corresponds to a signal such as the P wave or the T wave of the heartbeat signal, the maximum value M caused by a noise, and the like that are not suitable for the calculation of the number of pulses are not used as the targets of peak determination, and the maximum value M that corresponds to the R wave and is suitable for the calculation of the number of pulses is only used as the target of peak determination. Therefore, the calculation accuracy of the number of pulses is improved.

In addition, according to the measurement device 51 according to the present embodiment, the determination time T1 used for the determination of the peak value P is sequentially changed by the sequential change means in the processing operations in the steps 3 to 10, in response to the time interval T2 between the successive peak values P, as in the heartbeat signal Sf or the heartbeat signal Sg illustrated in FIG. 8, whose mutual values fall within a predetermined range and which have the peak values P greater than or equal to values obtained by subtracting the given value C from the peak values P occurring immediately before the peak values P.

Therefore, even in the case of the successive peak values P determined by the peak value determination means, when the mutual values thereof do not fall within the predetermined range, the successive peak values P are not regarded as the same type of peak value P, and the determination time T1 used for the determination of the peak value P is not changed in response to the time interval T2 between the peak values P. On the other hand, when the successive mutual peak values P fall within the predetermined range, the peak values P are regarded as the same type of peak value P, and the determination time T1 used for the determination of the peak value P is changed in response to the time interval T2 between the peak values P. Accordingly, the determination time T1 used for the determination of the peak value P is changed in response to the time interval T2 between the similar peak values P, and changed so as to accurately follow the transition of the number of pulses without being changed on the basis of the peak value P caused by a noise, or the like. As a result, the number of pulses of a living body, which sequentially fluctuates, turns out to be adequately calculated as needed, owing to the simplified arithmetic processing.

Figure 9:
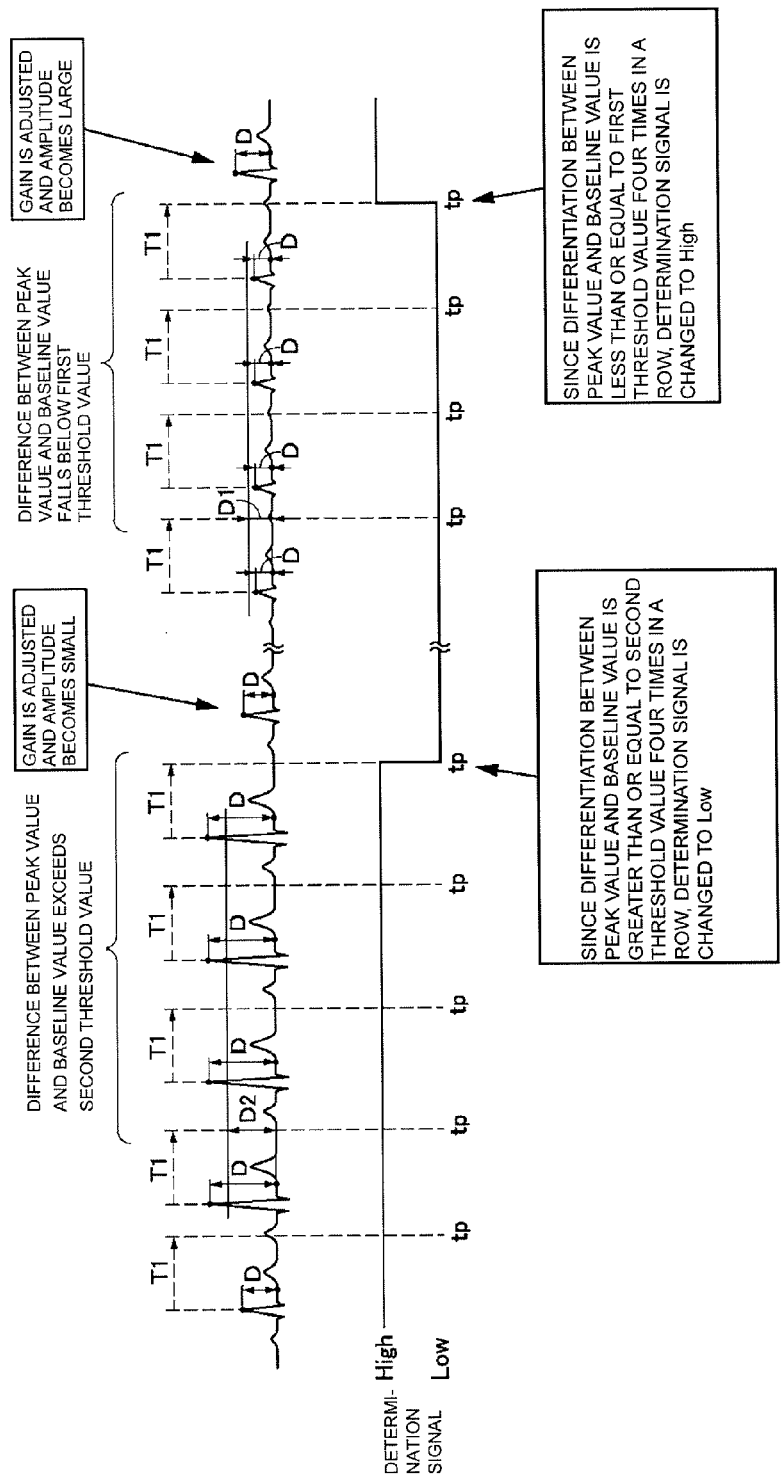
FIG. 9 is an explanatory diagram illustrating a heartbeat signal when an amplification factor is adjusted on the basis of a difference between a peak value and a baseline value.

In addition, according to the measurement device 51 according to the present embodiment, owing to the comparison means, in the steps 18 and 21, the difference D between the peak value P and the baseline value G is compared with the first threshold value D1 and the second threshold value D2, preliminarily set. In addition, when a state where the difference D between the peak value P and the baseline value G is larger than the second threshold value D2 has occurred four times in a row, the signal processing unit 57 outputs the determination signal Sj of the Low state, and the AGC circuit 58 outputs the feedback signal Vf causing the amplification factors of the first and second amplification units 53 and 54 to be decreased. On the other hand, when a state where the difference D between the peak value P and the baseline value G is smaller than the first threshold value D1 has occurred four times in a row, the signal processing unit 57 outputs the determination signal Sj of the High state, and the AGC circuit 58 outputs the feedback signal Vf causing the amplification factors of the first and second amplification units 53 and 54 to be increased. In this way, as illustrated in FIG. 9, even if the difference D between the peak value P and the baseline value G has changed, since the amplification factors of the first and second amplification units 53 and 54 are varied, it is possible to detect the differentially amplified signal V3 serving as the heartbeat signal in a suitable state.

Figure 11:
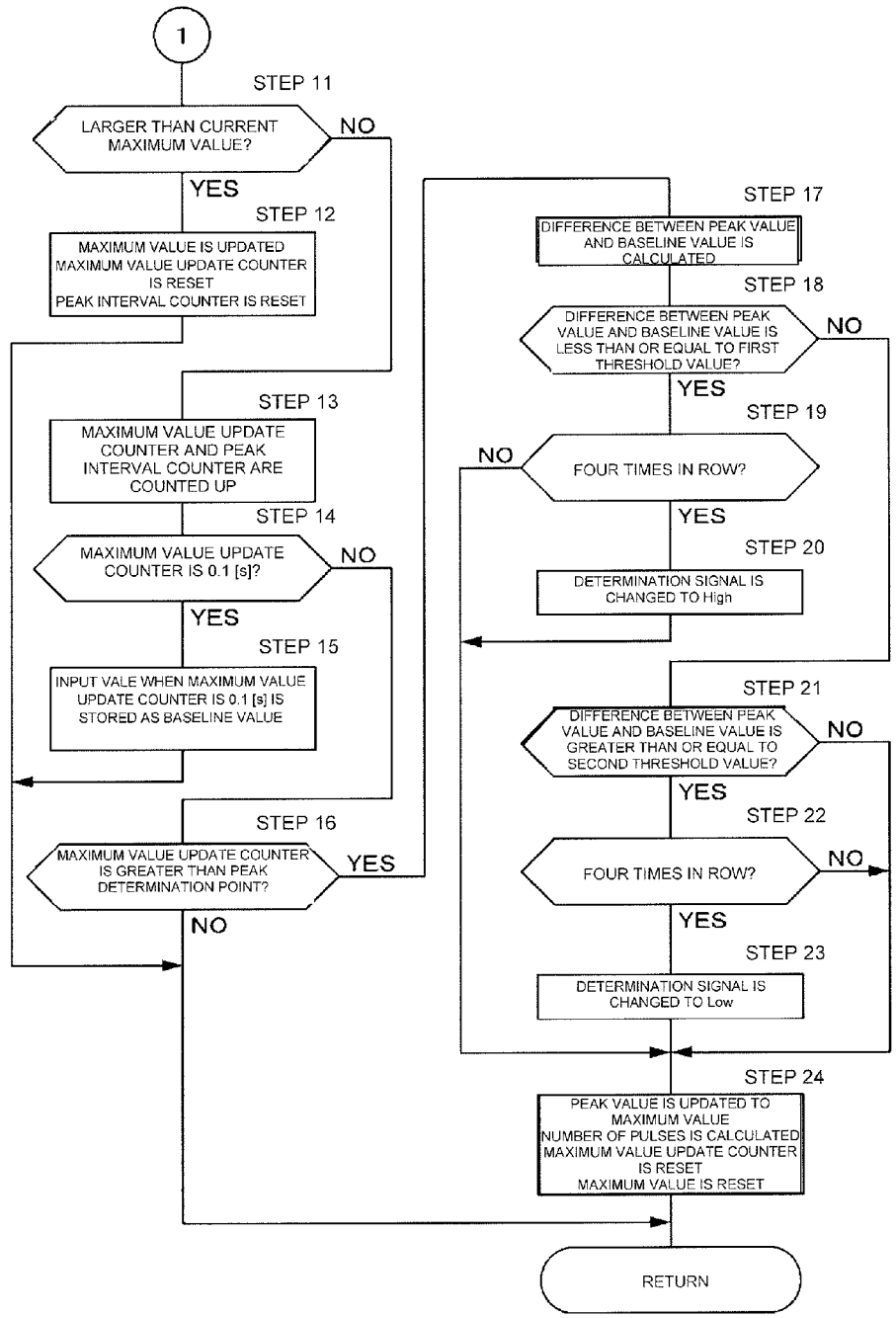

In addition, in the above-mentioned fourth embodiment, the step 1 in FIG. 10 indicates a specific example of the maximum value detection means, the steps 11 and 12 in FIG. 11 indicate a specific example of the determination time reset means, the step 16 and a portion in the step 24 that updates the peak value P in FIG. 11 indicate a specific example of the peak value determination means, and the steps 17 to 23 in FIG. 11 indicate a specific example of the comparison means. In addition, the steps 3 to 10 in FIG. 10 indicate a specific example of the sequential change means.

In addition, in the above-mentioned fourth embodiment, a configuration is adopted where, in the same way as the third embodiment, the AGC circuit 58 causes the resistance value of the variable resistance element 55 shared by the first and second amplification units 53 and 54 to change, and controls the amplification factors of the first and second amplification units 53 and 54 at the same time. However, the present invention is not limited to this, and the AGC circuit according to the fourth embodiment may also be applied to the second embodiment.

In addition, in the above-mentioned fourth embodiment, a configuration is adopted where, owing to the comparison means, the difference D between the peak value P and the baseline value G is compared with the two threshold values D1 and D2 and in response to this comparison result, the AGC circuit 58 switches the amplification factors of the first and second amplification units 53 and 54 in two stages. However, the present invention is not limited to this, a configuration may also be adopted where a difference between the peak value and the baseline value is compared with a single threshold value, and a configuration may also be adopted where a difference between the peak value and the baseline value is compared with three or more threshold values and the amplification factors of the first and second amplification units 53 and 54 are minutely switched in three or more stages.

In addition, while, in the above-mentioned fourth embodiment, a configuration is adopted where, owing to the sequential change means, the determination time T1 is sequentially changed in response to the time interval T2 between the peak values P, when, for example, a signal is detected where a time between peak values thereof is constant, a configuration may also be adopted where the sequential change means is omitted and the determination time is fixed to a given value within a range shorter than a time interval between the peak values.

In addition, in each of the above-mentioned embodiments, a configuration is adopted where the first and second detection electrodes 2 and 3 are directly attached to the living body surface. However, the present invention is not limited to this, for example a thin insulating film may be provided in the surface of a conductive film, and by causing the skin of a person to be measured and the conductive film to be capacitively coupled to each other across this insulating film, a detection signal may also be indirectly detected. In this case, it is desirable that the impedances of the first and second high impedance circuits 4 and 5 are set to 100 MΩ or more. In this way, it is possible to decrease a loss in 0.1 to 200 Hz serving as the frequency band of a living body signal and reduce the distortion of the living body signal, and it is possible to reduce the influence of a radiation noise containing, for example, the noise of a commercial power supply or the like.

In addition, in each of the above-mentioned embodiments, a configuration is adopted where the amplifier circuit 6 includes the first and second amplification units 7 and 8, the amplifier circuit 32 includes the first and second amplification units 33 and 34, the amplifier circuit 42 includes the first and second amplification units 43 and 44, the amplifier circuit 52 includes the first and second amplification units 53 and 54, and the separate detection electrodes 2 and 3 are connected to the input terminals of each of the amplification units. However, the present invention is not limited to this, and a configuration may also be adopted where three or more amplification units are provided in an amplifier circuit and separate detection electrodes are connected to the input terminals of each of the amplification units. In this case, using, for example, a selection switch or the like, a differential circuit selects two amplification units from among three or more amplification units, and differentially amplifies a difference between output signals from the selected amplification units.

In addition, while, in each of the above-mentioned embodiments, each of the first amplification units 7, 33, 43, and 53 and each of the second amplification units 8, 34, 44, and 54 are configured using the single operational amplifier 9 and the single operational amplifier 11, respectively, a configuration may also be adopted where multistage amplification is performed using a plurality of operational amplifiers.

In addition, while, in each of the above-mentioned embodiments, the operational amplifiers 9, 11, and 17 are configured using Op-amps, amplifying elements such as bipolar transistors or field-effect transistors may also be used.

In addition, while, in each of the above-mentioned embodiments, a configuration is adopted where the first and second output signals V1 and V2 are differentially amplified owing to the differential amplifier circuit 16, a configuration may also be adopted where a circuit is used that only operate a difference between the first and second output signals V1 and V2.

In addition, while, in the above-mentioned first to third embodiments, the arithmetic units 22, 37, and 46 including the A/D converter circuits 23 are connected on the subsequent stage sides of the differential amplifier circuits 16, the A/D converter circuits 23 may also be omitted and arithmetic units processing analog signals may also be connected.

In addition, in each of the above-mentioned embodiments, the amplification factors of the operational amplifiers 9 and 11 are set so that the first and second output signals V1 and V2 become values near to a maximum value of the driving voltage Vdd, within the range of the driving voltage Vdd. In addition, the amplification factors of the operational amplifiers 9 and 11 are set so that, within a range lower than the input level of the A/D converter circuit 23, the first and second output signals V1 and V2 become values near to the input level. However, the present invention is not limited to this, and the amplification factors of the operational amplifiers 9 and 11 may be arbitrarily set in response to a design specification or the like.

Furthermore, in each of the above-mentioned embodiments, cases are exemplified where the detection circuit of the present invention is applied to the measurement devices 1, 31, 41, and 51 for biological information, which detect the electrocardiographic signal of a person. However, the present invention is not limited to this, the present invention may also be applied to, for example, the detection of a muscle potential or the detection of a potential in the air, and the present invention may also be applied to various kinds of detection devices, each of which operates a difference between two detection signals.

REFERENCE SIGNS LIST 1, 31, 41, 51 measurement device
2 first detection electrode
3 second detection electrode
4 first high impedance circuit
5 second high impedance circuit
6, 32, 42, 52 amplifier circuit
7, 33, 43, 53 first amplification unit
8, 34, 44, 54 second amplification unit
9, 11, 17 operational amplifier
14 first coupling capacitor
15 second coupling capacitor
16 differential amplifier circuit (differential circuit)
22, 37, 46 arithmetic unit
23 A/D converter circuit
38, 47, 58 automatic gain control circuit (AGC circuit)
56 arithmetic unit (digital processing circuit)

The invention claimed is:
1. A detection circuit comprising:
a first detection electrode coupled to a first high impedance circuit;
a second detection electrode coupled to a second high impedance circuit;

an amplifier circuit including a first amplification unit configured to amplify a first detection signal received from the first detection electrode and a second amplification unit configured to amplify a second detection signal received from the second detection unit;

a differential circuit having a first input terminal configured to receive the first amplified detection signal and a second input terminal configured to receive the second amplified detection signal, the differential circuit being configured to output a differential signal between the first amplified detection signal and the second amplified detection signal;

a first coupling capacitor coupled between the first amplification unit and the first input terminal of the differential circuit; and a second coupling capacitor coupled between the second amplification unit and the second input terminal of the differential circuit, wherein the first high impedance circuit and the second high impedance circuit are coupled to a reference measurement electric potential.

2. The detection circuit according to claim 1, wherein the first amplification unit, the second amplification unit, and the differential circuit, each comprises at least one operational amplifier, respectively, and wherein the first amplification unit and the second amplification unit independently set amplification factors of the respective operational amplifiers such that, within driving voltage ranges that cause the respective operational amplifiers to operate, the first amplified detection signal and the second amplified detection signal are at respective voltage values substantially equal to a maximum value of the respective driving voltage ranges.

3. The detection circuit according to claim 1, further comprising a digital processing unit having an A/D converter coupled to an output terminal of the differential circuit.

4. The detection circuit according to claim 3, wherein the A/D converter has a predefined input level and is configured to apply the differential signal to the predefined input level to output a digital signal.

5. The detection circuit according to claim 4, wherein the first and second detection electrodes are configured to detect a pair of biological signals from a patient and the digital signal outputted from the digital processing unit represents biological information of the patient.

6. The detection circuit according to claim 1, further comprising an automatic gain control circuit configured to control a first amplification factor of the first amplification unit and a second amplification factor of the second amplification unit based on a feedback signal of the differential signal.

7. A detection circuit comprising:

a first detection electrode coupled to a first high impedance circuit;

a second detection electrode coupled to a second high impedance circuit;

an amplifier circuit including a first amplification unit configured to amplify a first detection signal received from the first detection electrode and a second amplification unit configured to amplify a second detection signal received from the second detection unit;

a differential circuit having a first input terminal configured to receive the first amplified detection signal and a second input terminal configured to receive the second amplified detection signal, the differential circuit being configured to output a differential signal between the first amplified detection signal and the second amplified detection signal; and a digital processing circuit coupled to an output terminal of the differential circuit and having:

an A/D converter circuit configured to convert the differential signal into a digital signal, and a processor configured to:

sequentially detect a maximum value in the digital signal for each of a plurality of successive sampling times, update the maximum value to a new maximum value of the digital signal when the new maximum value is larger than the maximum value during a determination time, reset the determination time from a time when the new maximum value is detected, and determine the maximum value as a peak value when no new maximum values are detected within the determination time, wherein the first high impedance circuit and the second high impedance circuit are coupled to a reference measurement electric potential.

8. The detection circuit according to claim 7, wherein the processor is further configured to compare a difference between the peak value and a reference value based on the reference measurement electric potential with at least one threshold value, wherein, when the difference between the peak value and the reference value exceeds the at least one threshold value, the automatic gain control circuit outputs the feedback signal to decrease the first and the second amplification factors, and wherein, when the difference between the peak value and the reference value is less than the at least one threshold value, the automatic gain control circuit outputs the feedback signal to increase the first and the second amplification factors.

9. The detection circuit according to claim 7, wherein the processor is further configured to sequentially change the determination time in response to a time interval between successive peak values.

10. The detection circuit according to claim 1, wherein the first amplification unit comprises a first operational amplifier and the second amplification unit comprises a second operational amplifier.

11. The detection circuit according to claim 10, wherein the first operation amplifier comprises a non-inverting terminal coupled to the first detection electrode and the second operation amplifier comprises a non-inverting terminal coupled to the second detection electrode.

12. The detection circuit according to claim 11, wherein the first and the second operation amplifiers each comprise an inverting terminal coupled to a resistance element.

13. The detection circuit according to claim 12, wherein the resistance element is a variable resistance element.

14. The detection circuit according to claim 1, wherein the first high impedance circuit and the second high impedance circuit are coupled to a connection point that is coupled to the reference measurement potential.

* * * * *